United States Patent
Lu et al.

(10) Patent No.: US 8,593,638 B2
(45) Date of Patent: Nov. 26, 2013

(54) SPLIT FREQUENCY SENSING METHODS AND SYSTEMS

(75) Inventors: Tao Lu, Victoria (CA); Tsu-Te Judith Su, Boca Raton, FL (US); Kerry J. Vahala, Pasadena, CA (US); Scott E. Fraser, La Canada, CA (US)

(73) Assignee: California Institute of Technology, Pasadena, CA (US)

( * ) Notice: Subject to any disclaimer, the term of this patent is extended or adjusted under 35 U.S.C. 154(b) by 709 days.

(21) Appl. No.: 12/573,009

(22) Filed: Oct. 2, 2009

(65) Prior Publication Data

US 2010/0085573 A1    Apr. 8, 2010

Related U.S. Application Data

(60) Provisional application No. 61/194,971, filed on Oct. 2, 2008.

(51) Int. Cl.
*G01B 9/02*    (2006.01)

(52) U.S. Cl.
USPC .......................................................... 356/480

(58) Field of Classification Search
USPC .......................................................... 356/480
See application file for complete search history.

(56) References Cited

U.S. PATENT DOCUMENTS

| | | | |
|---|---|---|---|
| 4,071,753 A | 1/1978 | Fulenwider et al. | |
| 4,419,895 A | 12/1983 | Fuller | |
| 5,343,490 A | 8/1994 | McCall | |
| 6,259,717 B1 | 7/2001 | Stone et al. | |
| 6,490,039 B2 | 12/2002 | Maleki et al. | |
| 6,657,731 B2 | 12/2003 | Tapalian et al. | |
| 6,741,628 B2 | 5/2004 | Painter et al. | |
| 7,003,002 B2 | 2/2006 | Vahala et al. | |
| 7,545,843 B2 | 6/2009 | Armani et al. | |
| 2002/0018611 A1 | 2/2002 | Maleki et al. | |
| 2005/0163185 A1 | 7/2005 | Vahala et al. | |
| 2005/0169331 A1 | 8/2005 | Vahala et al. | |
| 2007/0269901 A1 | 11/2007 | Armani et al. | |

(Continued)

FOREIGN PATENT DOCUMENTS

WO    WO 01/40757 A2    6/2001

OTHER PUBLICATIONS

Weiss, et al. "Splitting of high-Q Mie modes induced by light backscattering in silica microspheres." Optics Letters, vol. 20, No. 18, pp. 1835-1837 (1995) pp. 1835-1837. Sep. 15, 1995. (3 pages).

(Continued)

*Primary Examiner* — Tarifur Chowdhury
*Assistant Examiner* — Jonathan Hansen
(74) *Attorney, Agent, or Firm* — Vista IP Law Group LLP

(57) ABSTRACT

Resonant sensors and molecule detection methods utilizing split frequency. Optical energy is introduced into a microcavity, such as a toroid-shaped or spherical microcavity. A portion of the optical energy is backscattered and interacts with the introduced optical energy to form first and second modes of optical energy at respective first and second frequencies, also referred to as split frequency or mode doublets. One or more molecules bind to an outer surface of the microcavity and interact with an evanescent field of optical energy resonating within the microcavity. Binding of one or more molecules to the outer surface is detected based at least in part upon a change of the split frequency relative to a baseline split frequency.

30 Claims, 25 Drawing Sheets

(56) References Cited

U.S. PATENT DOCUMENTS

2009/0097031 A1 4/2009 Armani et al.
2009/0214755 A1 8/2009 Armani et al.
2009/0310140 A1* 12/2009 Smith et al. .................. 356/480

OTHER PUBLICATIONS

Gorodtsky, et al. "Rayleigh scattering in high-Q microspheres," Optical Society of America, vol. 17, No. 6, pp. 1051-1057 Jun. 2000 (7 pages).

Vollmer, et al. "Protein Detection by Optical Shift of a Resonant Microcavity". American Institute of Physics, Applied Physics Letters, vol. 80, No. 21. pp. 4057-4059. May 27, 2002. American Institute of Physics (3 pages).

D. Armani et al. "Ultra-high-Q toroid microcavity on a chip". Letters to Nature. Department of Applied Physics, California Institute of Technology, Pasadena CA. 2003 Nature Publishing Group. Nature, vol. 421, Feb. 27, 2003. pp. 925-928. (5 pages).

J. Niehusmann et al. "Ultrahigh-quality-factor silicon-on insulator microring resonator". Optics Letters vol. 29, No. 24. pp. 2861-2863, Optical Society of America, 2004. Dec. 15, 2004. (4 pages).

Ostby, E., Vahala, K., "Yb-doped glass microcavity laser operation in water," Optics Letters, vol. 34, No. 8, pp. 1153-1155 (Apr. 2009).

J. J Yao, et al "Silicon Microtoroidal Resonators with Integrated MEMS Tunable Laser". IEEE Journal of selected toopics in Quantum Electronics, vol. 13, No. 2. Mar./Apr. 2007. pp. 202-208.(2). (15 pages).

* cited by examiner

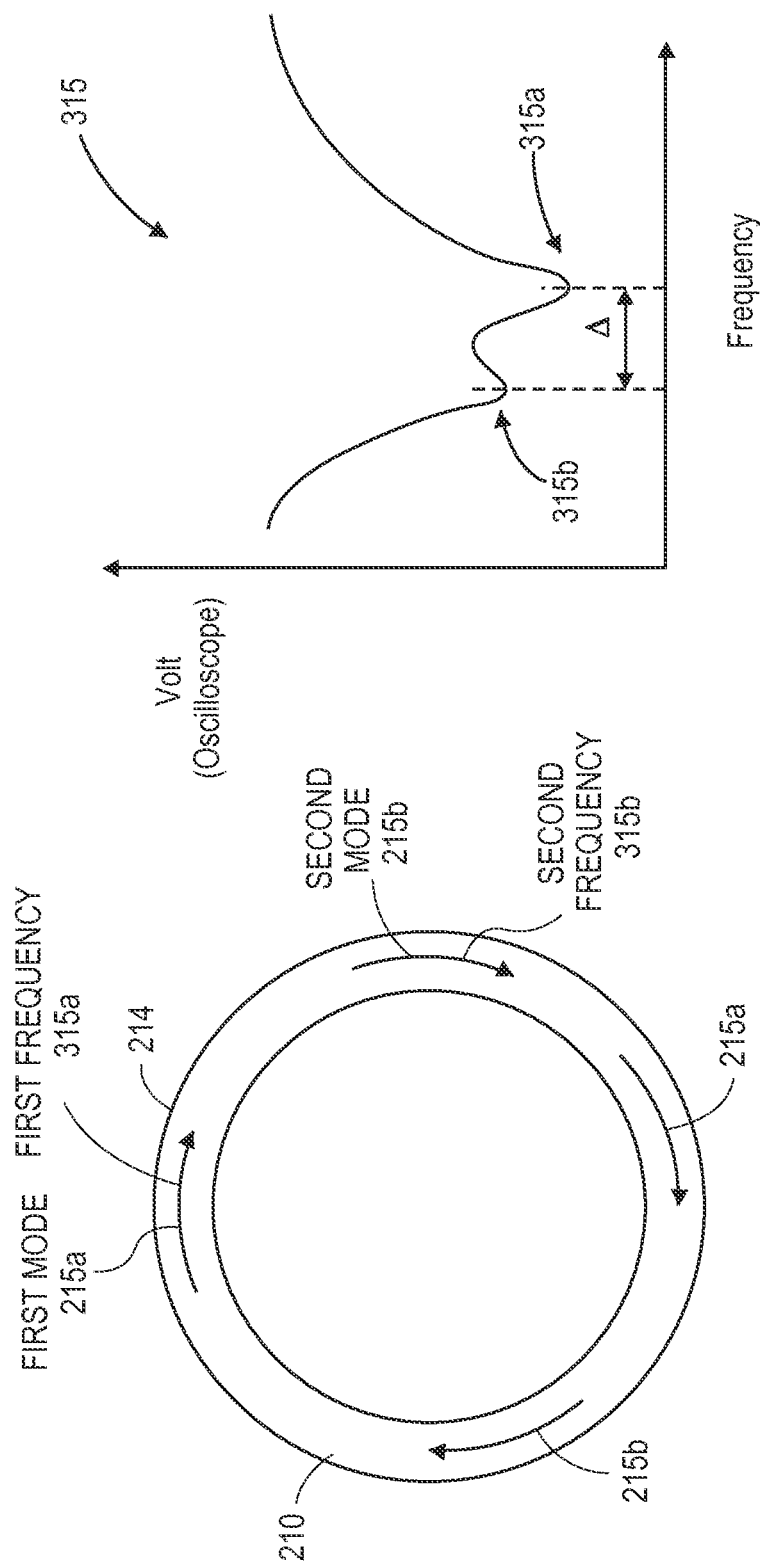

1) Photolithographically patterned silicon oxide disks are wet etched.

2) Silicon substrate is etched with $XeF_2$

3) $CO_2$ Layer activated with flow of the silicon oxide resulting in a toroid structure with an ultra-smooth surface

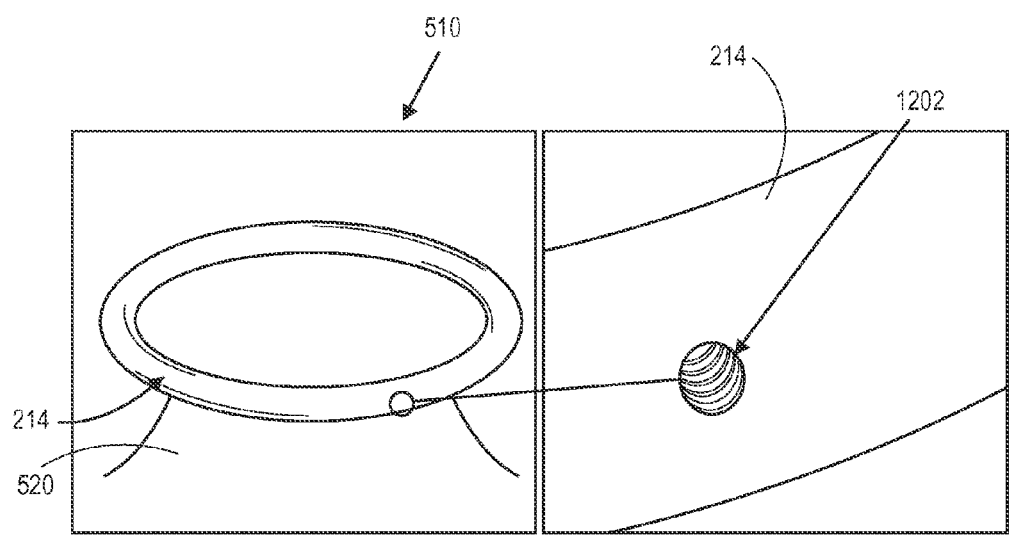
FIG. 12A  FIG. 12B

(b) Post injection of IL-2

Post-Glycine

SPLIT FREQUENCY SENSING METHODS AND SYSTEMS

CROSS-REFERENCE TO RELATED APPLICATION

This application claims the benefit under 35 U.S.C. §119 of U.S. Provisional Application Ser. No. 61/194,971, filed on Oct. 2, 2008, the entire contents of which are incorporated herein by reference as though set forth in full. This application is also related to U.S. Pat. Nos. 7,545,843, 7,781,217 and 8,107,081, the entire contents of which are also incorporated herein by reference as though set forth in full.

STATEMENT REGARDING FEDERALLY SPONSORED RESEARCH

The U.S. Government has certain rights in this invention pursuant to Grant No. HR0011-04-1-0032 awarded by DARPA.

FIELD OF THE INVENTION

The present invention relates to resonant microcavity sensors.

BACKGROUND

Known sensors for detecting small numbers of molecules and single molecules typically require a fluorescent or metallic label. In such systems, a label is attached to the target molecule so that the target molecule can then be identified by the sensor that detects that particular label. Such labels, however, require prior knowledge of the presence of the target molecule. Thus, known sensor systems that require labels are not suitable for blind detection of target molecules that do not have labels. Further, such labels may require additional data processing. As a result, label-based detection methods and devices may not be suitable for real-time processing and are not suitable for detection of small numbers of unlabeled molecules including unlabeled single molecules.

Label-free molecule detectors have been an active research area due to the demand for reliable detection of low concentration biological agents, particularly label-free detectors for detecting small numbers of molecules and single molecules. Several devices have been proposed or utilized for label-free detection including fiber optic waveguides, nanowires, nanoparticle probes, biochips, mechanical cantilevers and microsphere resonators. U.S. Pat. Nos. 4,071,753 to Fulenwider et al. and 4,419,895 to Fuller describe sensors that utilize optical fibers. Another type of optical sensor involves modulation of vibrational motion of a transducer, which changes the intensity of light coupled between the ends of two optical fibers so that by measuring such changes the physical parameter can be detected and measured.

U.S. Pat. No. 6,583,399 to Painter et al. describes a microsphere resonant sensor that includes a modifier that is bound to an outer surface of the resonator. The modifier provides a binding site such that a binding event occurs at the outer surface of the micro-sphere in the presence of a target molecule. U.S. Publication No. 2007/0269901 A1 describes label-free sensing methods that involve a thermo-optic effect and monitoring how the resonance wavelength of the microcavity shifts when molecules bind to the outer surface of the microcavity. Molecules that bind to an outer surface of a microcavity interact with an evanescent field generated by optical energy resonating within the microcavity, thereby resulting in heating of the microcavity, which alters the index of refraction and resonance wavelength.

While certain known devices may be utilized for label-free detection, they can be improved. Certain known sensors do not have sufficient sensitivity to allow detection of a very small number of molecules or a single molecule. These low sensitivity sensors may not be suitable for biological and chemical analyses that require higher sensitivities such as cell signaling and cellular dynamics and various environmental applications. The reasons for inadequate sensitivities are specific to each type of sensor. For example, sensitivities of sensors having mechanical components may be limited given the particular mechanical construct.

Certain known devices may also have other limitations. For example, in the case of certain optical sensors and traps, sensitivity limitations are due, in part, to the limited interaction of light with the target molecule. Further, the reliability and sensitivity of other sensing methods, such as methods that monitor resonance wavelength, may be affected by the optical path fluctuation within the microcavity due to factors such as temperature variations, turbulence that is induced by injection of bio-fluids into the microcavity environment and frequency jittering of a laser source coupled to the microcavity.

Various sensors also present manufacturing and integration challenges that limit the extent to which the devices can be used on a large-scale basis. Further, in the case of optical sensors, it is necessary to increase the evanescent field intensity to increase the detection limit into the single molecule regime, but many optical sensors are not physically capable of such intensity increases.

SUMMARY

One embodiment is directed to a method of detecting at least one molecule in an environment, which may be a gaseous or liquid environment. The method comprises introducing optical energy into a microcavity such that the optical energy resonates within the microcavity. The method further comprises detecting at least one molecule, including detection of a single molecule, which binds to an outer surface of the microcavity. Detection is based at least in part upon a change of a difference between first and second frequencies of respective first and second modes of optical energy resonating within the micro-cavity, also referred to as split frequency or mode doublets, which may be caused by coherent interaction of counter-propagating modes of optical energy, due to the at least one molecule binding to the outer surface.

Another embodiment is directed to a method of detecting at least one molecule, including a single molecule, and comprises introducing optical energy into a resonant microcavity having a functionalized outer surface. A first mode of optical energy at a first frequency and a second mode of optical energy at a second frequency circulate within the resonant microcavity. The method further comprises determining a baseline frequency difference. The baseline frequency difference comprises a difference between the first and second frequencies due to an intrinsic property of the resonant microcavity and before a molecule binds to the outer surface. The method further comprises monitoring a difference between the first and second frequencies and detecting at least one molecule that binds to the functionalized outer surface based at least in part upon how the detected difference between the first and second frequencies changes relative to the baseline difference due to binding of one or more molecules to the outer surface.

Another embodiment is directed to a system for detecting at least one molecule, including a single molecule, in an environment such as a gaseous or liquid environment. The system comprises a resonant microcavity, a waveguide positioned to couple optical energy from a source into the resonant microcavity, a detector arranged to sense optical energy that evanesces beyond an outer surface of the resonant microcavity and a controller or other processing element that receives data from the detector. Data from the detector is related to optical energy having first and second frequencies as a result of coherent interaction of counter-propagating modes of optical energy, otherwise referred to as split frequency or mode doublets. The controller or processing element is configured or operable to detect at least one molecule that binds to an outer surface of the microcavity based at least in part upon how a difference between first and second frequencies of respective first and second modes of optical energy changes, or how the split frequency changes, due to the at least one molecule binding to the outer surface.

A further embodiment is directed to a system for detecting at least one molecule in an environment such as a gaseous or liquid environment. The system comprises a resonant microcavity having a functionalized outer surface, a waveguide positioned to couple optical energy into the resonant microcavity, a detector arranged to sense optical energy that evanesces beyond an outer surface of the resonant microcavity and a controller or other processing element that receives data from the detector. Data received from the detector is related to first and second modes of optical energy at respective first and second frequencies, also referred to as split frequency or mode doublets, which may be caused coherent interaction of counter-propagating modes of optical energy. The controller or processing element is configured or operable to determine a baseline difference comprising a difference between the first and second frequencies due to an intrinsic property of the microcavity before a molecule binds to the outer surface and monitoring the first and second frequencies. The controller or processing element is also configured or operable to detect at least one molecule that binds to the functionalized outer surface based at least in part upon how the detected difference between the first and second frequencies, or the split frequency, changes relative to the baseline difference due to binding of one or more molecules to the outer surface.

In one or more embodiments, optical energy is introduced into a microcavity and is at a resonance frequency and circulates in a forwards direction within the microcavity. A portion of the optical energy is backscattered and circulates in a backwards direction within the resonant microcavity. Optical energy introduced into the microcavity and circulating in a forwards direction and backscattered optical energy circulating in a backwards direction interact with each other to form coherent optical energy having first and second resonant frequencies, or split frequency or mode doublets, resonating in both directions. Detected changes of the difference between the first and second frequencies, or how this split frequency changes, are compared to baseline frequency differences to detect molecules on the outer surface. In one or more embodiments, split frequency changes are compared to a baseline frequency difference which, in certain embodiments, is a difference between the respective frequencies of the first or second modes, or split modes, before a molecule binds to the outer surface, e.g., due to intrinsic, material or structural properties of the microcavity such as one or more or all of Rayleigh scattering, a shape irregularity (e.g., a degree of ellipticity), a material impurity and a micro-defect of the microcavity.

In one or more embodiments, one of the modes is a result of interaction of backscattered optical energy and optical energy introduced into the microcavity. More particularly, at least one of the first and second modes of optical energy is generated as a result of optical energy being introduced into the microcavity, at least a portion of the introduced optical energy backscattering, and the introduced and backscattered optical energy interacting with each other to form at least one of the first and second modes.

Formation of backscattered energy and split frequency may, in certain embodiments, be caused by an intrinsic microcavity property or induced. For example, prior to binding of molecules to the microcavity, backscattering may result from an intrinsic property, irregularity or defect of the microcavity (e.g., a defect or irregularity formed during fabrication of the microcavity). In other embodiments, an irregularity or defect is intentionally formed within the microcavity to induce backscattering. In certain embodiments, for this purpose, a focused ion beam or other source of energy may be applied to the outer surface of the microcavity to foam an aperture, divot, hole or other defect within the microcavity. The divot may, for example, be formed using about a 10 pA focused ion beam for about five seconds, which can form a divot having a diameter of about 50 nm. Optical energy that is introduced into a microcavity having such a divot circulates in the microcavity, a portion of which is backscattered due in part to the divot, and the introduced optical energy and the backscattered optical energy induced by the aperture or divot interact to form optical energy having first and second modes at respective first and second frequencies.

Embodiments may be utilized to detect labeled molecules and for label-free detection of various numbers and types of molecules that bind to the outer surface. Embodiments may also be utilized for detection of a single unlabeled molecule. The magnitude of the difference between the respective frequencies increases as additional molecules bind to the outer surface. For this purpose, the detection of unlabeled molecules may be performed utilizing a microcavity having a functionalized outer surface such as an antibody, an antigen or a protein, for detection of various chemical and biological molecules. Given the manner in which embodiments function, detection is insensitive to factors that may affect reliability and sensitivity such as frequency jitter of a source of the optical energy, temperature variations and turbulence due to fluid injection since these effects are essentially canceled due to the split frequency modes caused by interaction of forwards and backscattered optical energy being subjected to the same factors.

Embodiments may involve a passive resonant microcavity, such as an undoped planar microcavity, examples of which include a spherical microcavity and a planar microcavity that is supported by a substrate such as a toroid-shaped microcavity supported by a substrate. In such devices, an outer edge of the planar, toroid-shaped microcavity extends outwardly beyond an outer edge of the substrate. These types of devices may have high and ultra-high Q values (greater than $10^8$) to provide very high sensitivities to detect very small numbers of molecules, including a single molecule.

Embodiments may also utilize active components such as microcavity lasers such as toroid lasers. These types of devices output split modes or first and second frequencies and also have sufficient sensitivities to detect small numbers of molecules, including a single molecule. For example, embodiments may involve a microcavity laser such as an ytterbium-doped silica microcavity laser that may, in certain embodiments, have a toroid shape and operate within a liquid environment such as water.

In one or more embodiments, the change between the first and second frequencies, or the change of the split frequency, may be a result of one or more or all of a cavity linewidth or Q value and control techniques. The difference between frequencies can be expressed as follows:

$$\beta = \frac{\omega_0}{2} \frac{\int \sum_i \delta \in (r_i) E_+ E_-^* dv}{\int \in (r_i) E_+ E_+^* dv} + \beta_0$$

wherein $\beta$ is the difference between the first and second frequencies of respective first and second or split modes due to binding of at least one molecule to the outer surface, $\beta_0$ is a baseline split frequency or baseline difference between the first and second frequencies of respective first and second modes due to an intrinsic property of the microcavity (prior to binding of a molecule to the outer surface), $\delta\in(r_i)$ is a change of relative permittivity of the microcavity due to the at least one molecule binding to the outer surface at a spatial position $r_i$, $E_+$ is a first propagation mode, $E_+^*$ is a complex conjugate of the first mode, and $E_-^*$ is a complex conjugate of a second propagation mode.

BRIEF DESCRIPTION OF THE DRAWINGS

Referring now to the drawings in which like reference numbers represent corresponding parts throughout and in which:

FIG. 3 generally illustrates a top view of a micro-cavity and first and second modes of optical energy, or split modes, having respective first and second frequencies;

FIG. 4 is a graph generally illustrating split frequency or mode doublets resulting from interaction of optical energy introduced into a microcavity and backscattered optical energy;

FIGS. 12A-F illustrate one embodiment directed to inducing split frequency modes by forming an aperture, divot or defect within an outer surface of a micro-cavity;

DETAILED DESCRIPTION OF ILLUSTRATED EMBODIMENTS

Figure 1:
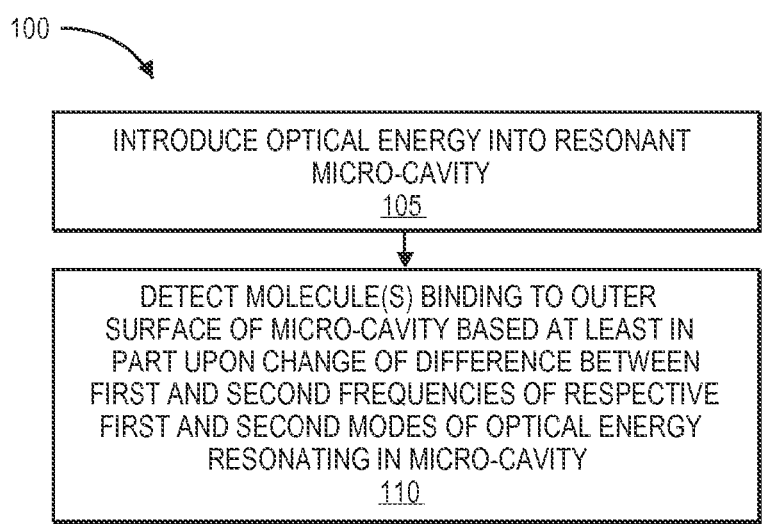
FIG. 1 is a flow chart of one embodiment of a method for detecting one or more molecules that bind to an outer surface of a resonant micro-cavity utilizing split frequency analysis.
Figure 2:
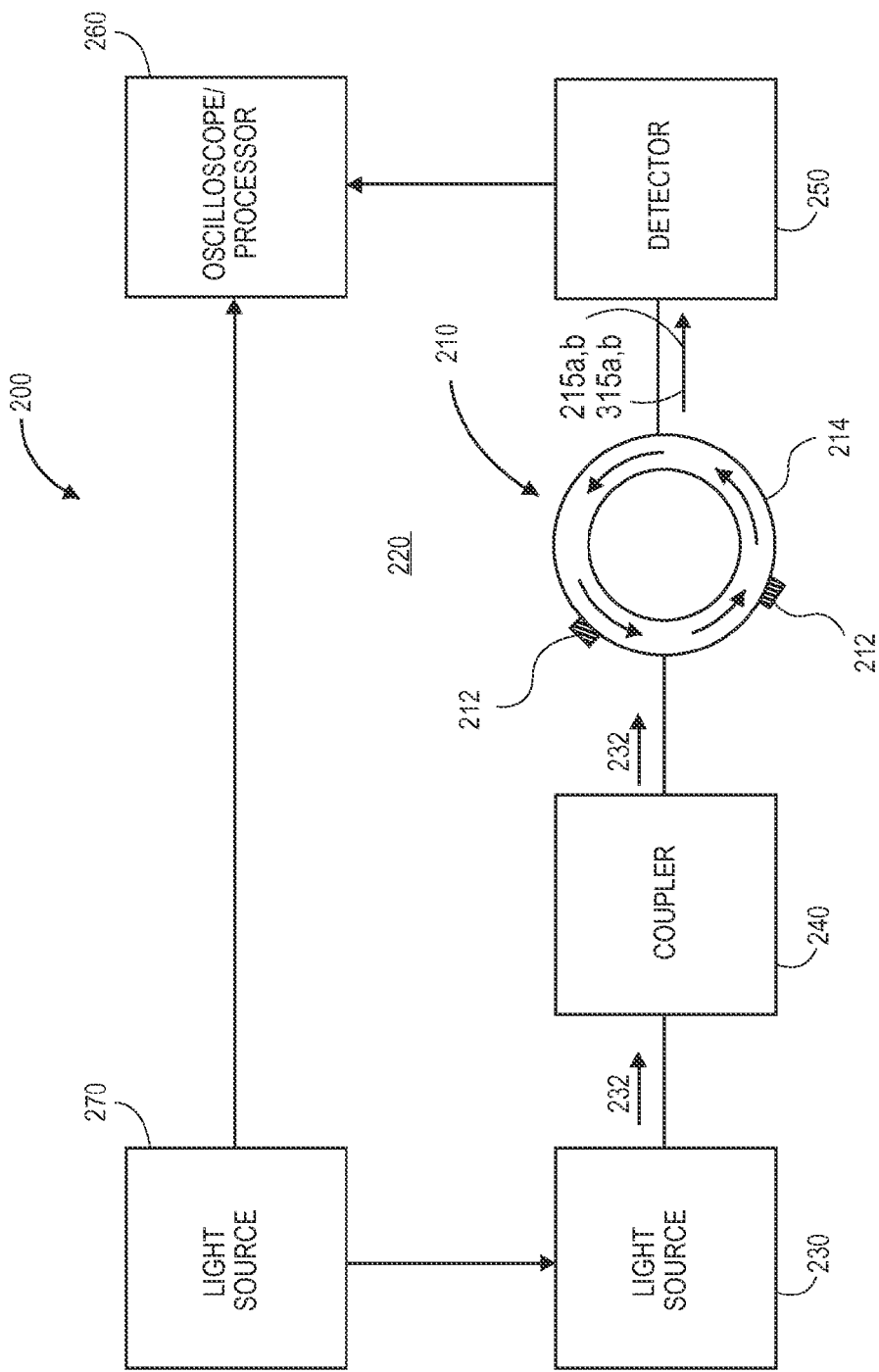
FIG. 2 is a block diagram of a system constructed according to one embodiment for detecting one or more molecules that bind to an outer surface of a resonant micro-cavity utilizing split frequency analysis.

Referring to FIGS. 1-4, embodiments are directed to sensing methods 100 and systems 200 that utilize split frequencies 315a and 315b (generally, 315), otherwise referred to as split frequency or mode doublets, of respective first and second modes 215a and 215b (generally, 215) of optical energy 232 resonating within a microcavity 200 to determine how many molecules 212 bind to an outer surface 214 of a resonant microcavity 210. In one embodiment, a method 100 of detecting a molecule 212 in an air or liquid environment 220 includes, at step 105, introducing optical energy 232 from a source 230 and into the resonant microcavity 210, and at step 110, detecting one or more molecules 212 that bind to the outer surface 214 of the microcavity 210 based at least in part upon a change of a difference between first and second frequencies 315a and 315b of respective first and second modes 215a and 215b. Thus, embodiments function in a manner that is different compared to other microcavity sensors and sensing methods, for example, other systems and methods that utilize a thermo-optic effect and monitoring how the resonance wavelength of the microcavity shifts when molecules bind to the outer surface of the microcavity.

Embodiments can be implemented utilizing micro-cavities 210 including ultra-high Q microcavity resonators and functionalized outer surfaces 214 to provide high sensitivity and selectivity. These capabilities are provided by embodiments while reducing or eliminating factors such as laser jitter, temperature fluctuations and turbulence due to fluid injections that may reduce the sensitivity or reliability of certain known microcavity sensor devices as a result of embodiments utilizing data of first and second modes 215a, 215b of optical energy 232 that are the result of or are generated by interaction of counter-propagating modes (discussed in further detail below). Thus, these sensitivity reducing factors are effectively negated or canceled out, whereas they may affect how other known devices operate. Embodiments provide these capabilities and advantages while being able to detect labeled and label-free molecules 212, e.g., utilizing functionalized microcavity surfaces 214, in various environments 220 including air and water. Embodiments can also be implemented using various types and shapes of micro-cavities 210. Further aspects of embodiments are described below with reference to FIGS. 2-15H, which show by way of illustration specific embodiments in which the invention may be practiced.

Referring again to FIGS. 2-4, a system 200 for performing the method 100 shown in FIG. 1 and other methods and steps thereof described with reference to other figures includes the source 210 of light or optical energy 212 such as a laser or other suitable source 230, a coupler 240 adapted to receive optical energy 232 from the source 230 and to couple optical energy 232 into the microcavity or microresonator 230 that is optically coupled to the coupler 240, and one or more detectors 250 such as a photo-detector that is adapted to observe or receive as an input optical energy that exits or evanesces from the microcavity 210. Embodiments can be implemented using various couplers 240 and microcavities 210, and the coupler 240 and microcavity 210 may be individual components that are positioned when the sensor system 200 is to be used, or they may be part of a manufactured package of components. The output of the detector 250 is provided to a display, processor or other element 260 for determining the magnitude of the split frequency, i.e., the difference between split frequencies 315a, 315b (or the two "dips" as shown in FIG. 4) of respective first and second modes 215a, 215b of optical energy.

For this purpose, a function generator 270 is operably coupled to the light source 230 and to the display or processor 260 (such as an oscilloscope) to scan wavelengths of the source 230 and to detect, with the oscilloscope 260, power that is transmitted out of the micro-cavity 210 in synchronization with the waveform generated by the function generator 270. In this manner, each point of a time axis on an display of the oscilloscope 260 represents a distinct wavelength or optical frequency, and with further reference to FIGS. 3-4, the two dips 315a, 315b of the split frequency of respective first and second modes 215a, 215b appear on the oscilloscope 260 or are otherwise processed such that the distance between these two dips 315a, 315b indicates the split frequency difference. Embodiments detect changes of the split frequency difference 315 and determine how many molecules 212 have bound to the outer surface 214 of the microcavity 210 based at least in part upon these changes.

Figure 5:
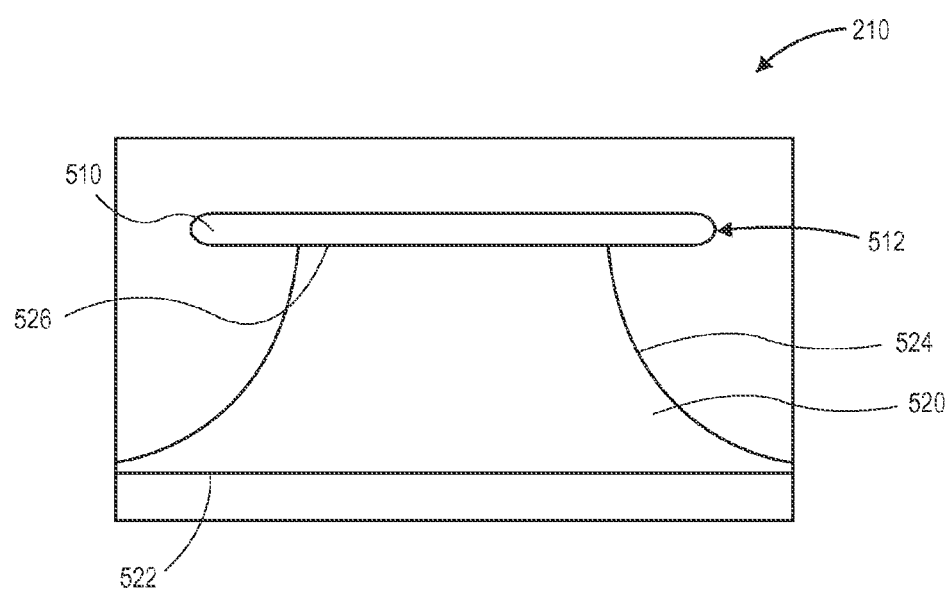
FIG. 5 is a side view of a toroid-shaped microcavity that may be utilized in embodiments.
Figure 6:
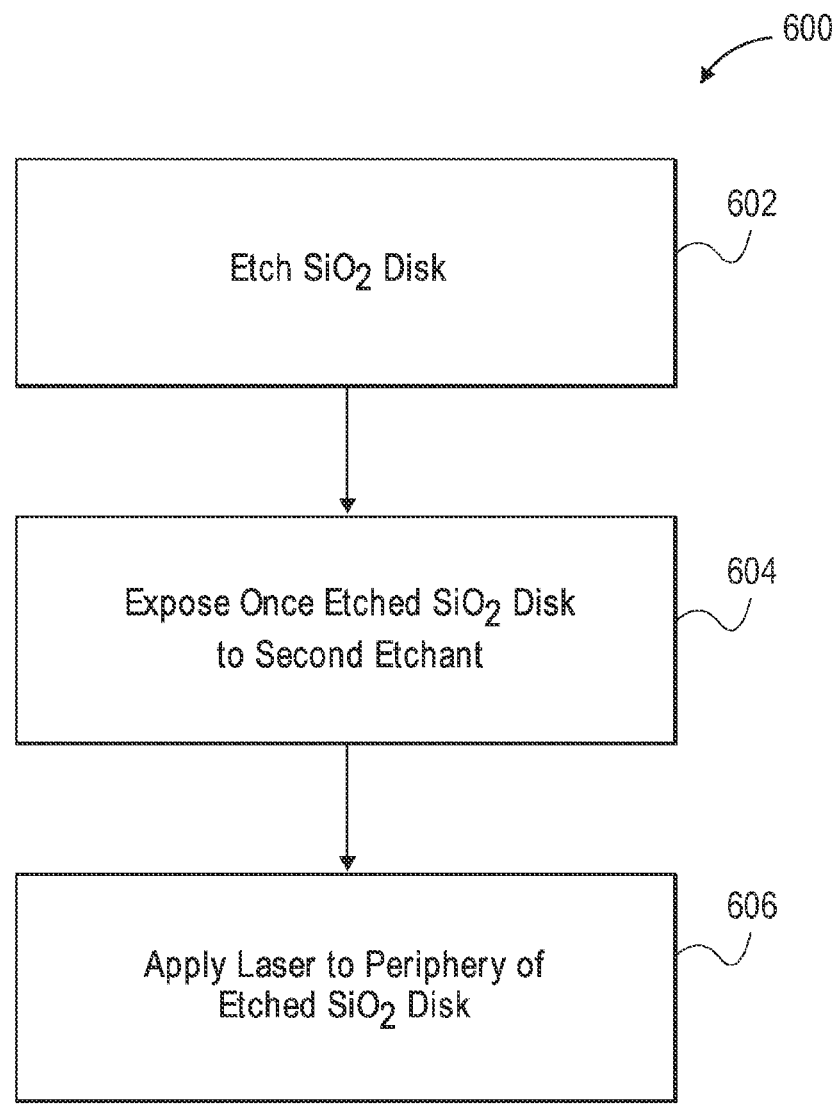
FIG. 6 is a flow diagram illustrating a method of fabricating a toroid-shaped microcavity that may be utilized in embodiments.

Referring to FIG. 5, one resonant microcavity 210 that may be utilized in embodiments is in the form of a ring, a disk or a toroid 510 (generally referred to as toroid-shaped microcavity 510 or microcavity 510). In the illustrated example, a toroid-shaped microcavity 510 is supported by a substrate 520. The toroid-shaped microcavity 510 can be a silica resonant microcavity, and the substrate 520 can be a silicon substrate. It should be understood that other microcavity 510 and substrate 520 materials may be utilized. With embodiments having these materials, microcavity resonator and sensor embodiments can be implemented utilizing a single or multiple micro-cavities 510 that may be on a silicon chip.

In the toroid-shaped microcavity 510 shown in FIG. 5, the substrate 520 includes a bottom surface 522, a middle tapered or angled surface 524, and a top surface 526. Portions of the silicon substrate 520 that are located below the microcavity 510, e.g., below a periphery 512 of the microcavity 510, are removed or etched away such that the substrate 520 is in a form of a support pillar, and the inner edge of the microcavity 510 extends around the outer edge of the top surface 526 of the substrate 520. Thus, the substrate 520 effectively supports and elevates the microcavity 510 above the bottom surface 522 of the substrate 520. In the illustrated embodiment, the microcavity 510 is substantially parallel to a top surface 526 of the pillar, but non-parallel orientations may also be utilized.

Optical energy 232 introduced into the microcavity 510 from the source 230 travels along an inner surface of the outer edge of the microcavity 510, for example, within a whispering gallery mode (WGM) or other resonant modes. A WGM is a resonant mode in which waves of optical energy 232 are totally internally reflected, and focused by the inner surface of the microcavity 510. Thus, the optical energy can circulate within the microcavity 510 and be confined therein to provide high and ultra-high Q values, as described in further detail in U.S. Pat. No. 7,545,843 and U.S. application Ser. Nos. 11/733,480 and 12/243,580, the contents of which were previously incorporated herein by reference.

In one embodiment, the diameter of a silica microcavity 510 is about 10 µm to about 500 µm, preferably between 15 µm to about 200 µm, and the corresponding Q values can range from about $10^4$ to about $10^9$. In one embodiment, an ultra-high Q microcavity 510 has a diameter of at least about 10 µm, e.g., between about 10 and about 30 µm, and a Q value of about 500 million.

It should be understood that the size of the microcavity 510 can vary and the Q value can vary, and that embodiments of the invention are capable of supporting optical energy 232 at various Q values including "high" Q values and even higher Q values, such as "ultra-high" Q values. For example, the in embodiments of the present invention, the microcavity 510 may have high Q values of at least $10^6$ or one million and ultra-high Q values of about $10^8$ or 100 million to about $5 \times 10^8$ or 500 million.

Figure 7A:
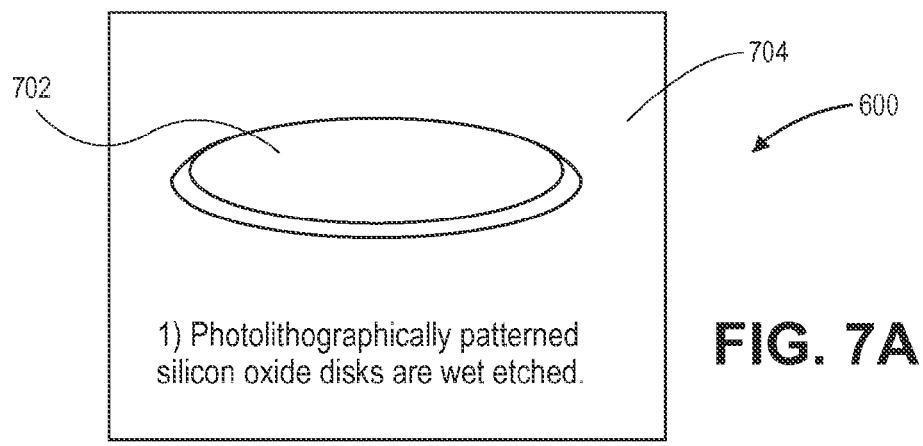
FIGS. 7A-C graphically illustrate a method of fabricating a toroid-shaped microcavity as shown in FIG. 6.
Figure 7B:
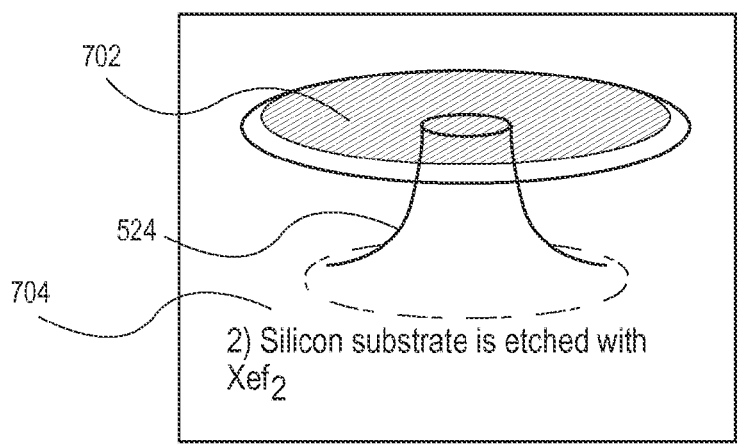
Figure 7C:
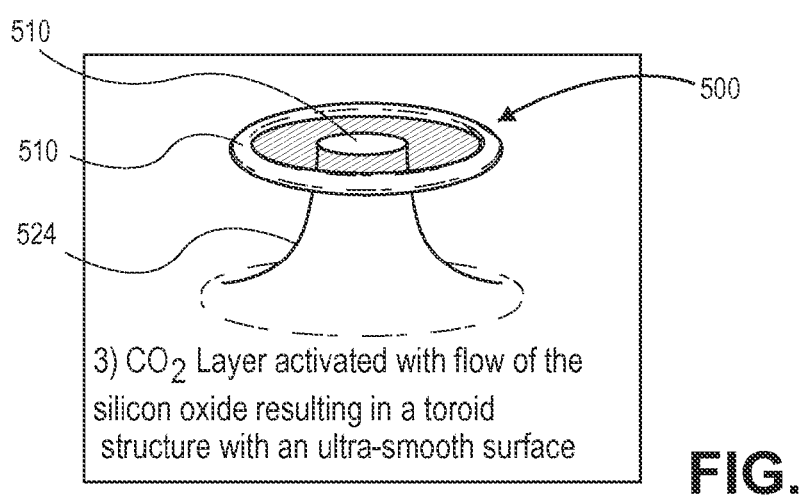

FIGS. 6 and 7A-C illustrate one method 600 of fabricating a toroid-shaped microcavity 510, such as an ultra-high Q microcavity that may be utilized in embodiments. Initially, in step 602, a silica or silicon dioxide ($SiO_2$) disk or a circular pad 702 is etched, e.g. on a silicon substrate 704 (as shown in FIG. 7A), for example, with a hydrogen fluoride (HF) solution. In step 604, the silica disk 702 is exposed to a second etchant, such as xenon difluoride ($XeF_2$) gas, which removes portions of the silicon base beneath the periphery of the silica disk 702 (as shown in FIG. 7B). In step 606, a laser, such as an Excimer or $CO_2$ laser, is applied to the undercut periphery of the silica disk 702 (as shown in FIG. 7C). As a result of the laser illumination, the periphery portions of the silica disk 702 are melted or partially or completely liquefied, and a toroid-shaped microcavity 510 is formed. Further details of fabrication steps and aspects thereof are described in U.S. Pat. No. 7,545,843 and "Ultra-High-Q Toroid Microcavity on a Chip," Nature, vol. 421, no. 6926, pp. 925-928 (Feb. 27, 2003), the contents of which are incorporated herein by reference.

Figure 8A:
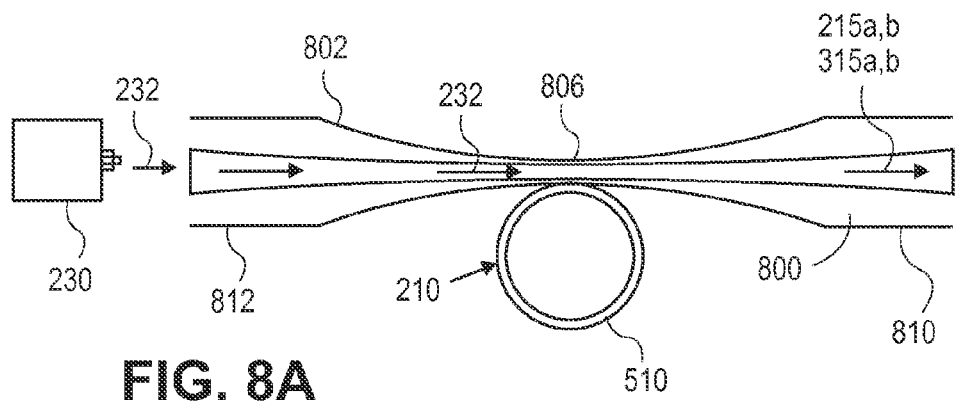
FIGS. 8A-C are different views of a fiber taper coupler or waveguide that may be used in embodiments to couple optical energy into a micocavity.
Figure 8B:
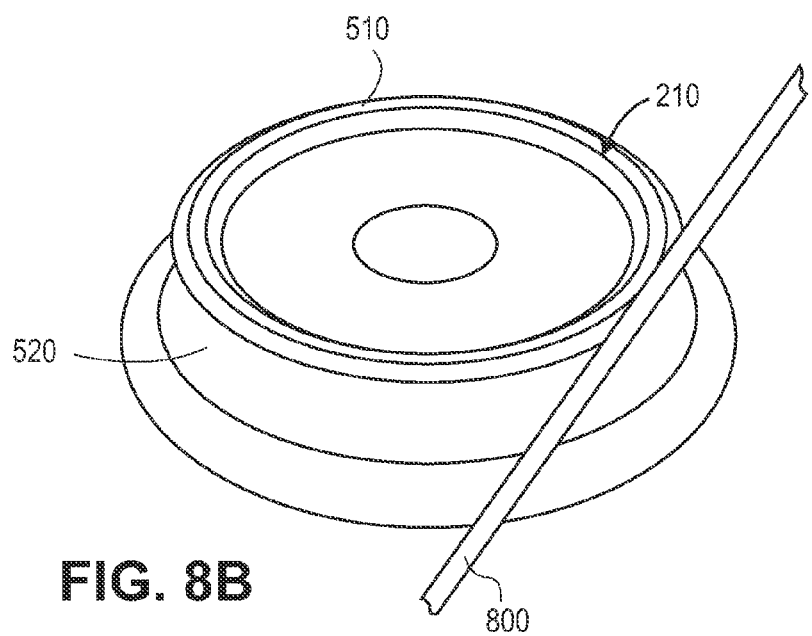
Figure 8C:
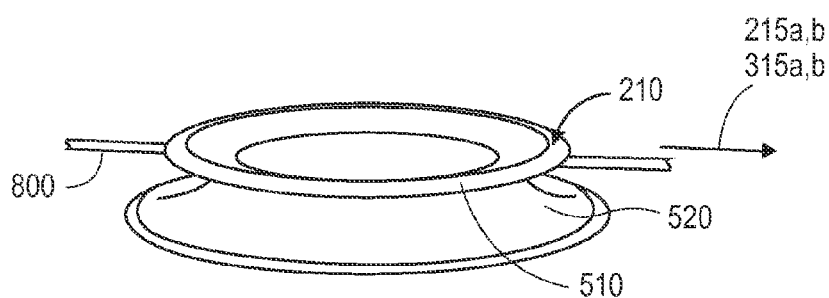

One manner in which light stored in a resonant microcavity 210 is coupled to a transmission media, waveguide or coupler 240 is illustrated in FIGS. 8A-C. Transmission media 800 is utilized to carry optical energy 232 that is to be stored or resonate in the microcavity 210. Active media, which are excited by optical pumps can also be associated with the micro-cavities 210 to facilitate the lasing of a signal within a frequency band of interest. In one embodiment, as illustrated in FIGS. 8A-C, the transmission media 800 is a fiber waveguide, preferably a tapered waveguide as shown in FIG. 8A, although other waveguide configurations can also be utilized. One suitable tapered fiber waveguide 800 has tapered sections 802 and 804 and the intermediate waist region 806 of the waveguide 800 may be provided, as is known, by stretching a fiber (e.g., a single mode fiber) under controllable tension as it is softened by one or more fixed or movable heat sources (e.g., torches). The microcavity 210 is coupled to the externally guided power about the waist region 806 of the fiber 800. Commercially available machines can be used for this purpose in production environments. Taper waist 806 diameters are typically several microns, preferably about two microns. The diameter of the waist region can be adjusted to properly phase-match to the ultra-high Q microcavity resonator.

The consequent reduction in diameter of about one or more orders of magnitude reduces the central core in the core/cladding structure of the optical fiber 800 to vestigial size and function. As a result, the core no longer propagates a majority of the wave energy. Instead, without significant loss, the wave power in the full diameter fiber 800 transitions into the waist region 806, where power is confined both within the attenuated cladding material and within a field emanating into the surrounding environment. After propagating through the waist region 806, exterior wave power is recaptured in the diverging tapered region and is again propagated with low loss within the outgoing fiber section 810.

An optical pump or source 230 of optical energy 232 is optically connected to a first end 812 of the fiber 800. The optical pump 820 transmits a signal along the waveguide and to the microcavity 210 through the fiber taper. One or more excited laser signals in the microcavity 210 are then communicated to the fiber waveguide 800. The microcavity 210 recirculates the energy with low loss in, for example, a WGM or other resonant mode, returning a part of the power to the waveguide 800 at the waist 806.

When a resonance exists at the chosen wavelength, the microcavity 210 functions with effectively total internal reflection and with minimal internal attenuation and radiative losses. However, the emanating portion of the wave power is still confined and guided, so it is presented for coupling back into the waveguide waist 806. These fiber coupling techniques can be used to couple a single tapered fiber to a microcavity 210, as shown in FIGS. 8A-C. Alternatively, a plurality of tapered fibers can be coupled to a plurality of microcavities 210, for example, as part of a circuit or to integrate with other components. Other characteristics and technical aspects of couplers that may be utilized in embodiments are described in U.S. Pat. Nos. 7,545,843, 7,781,217 and 8,107,081, the contents of which were previously incorporated herein by reference.

Figure 9:
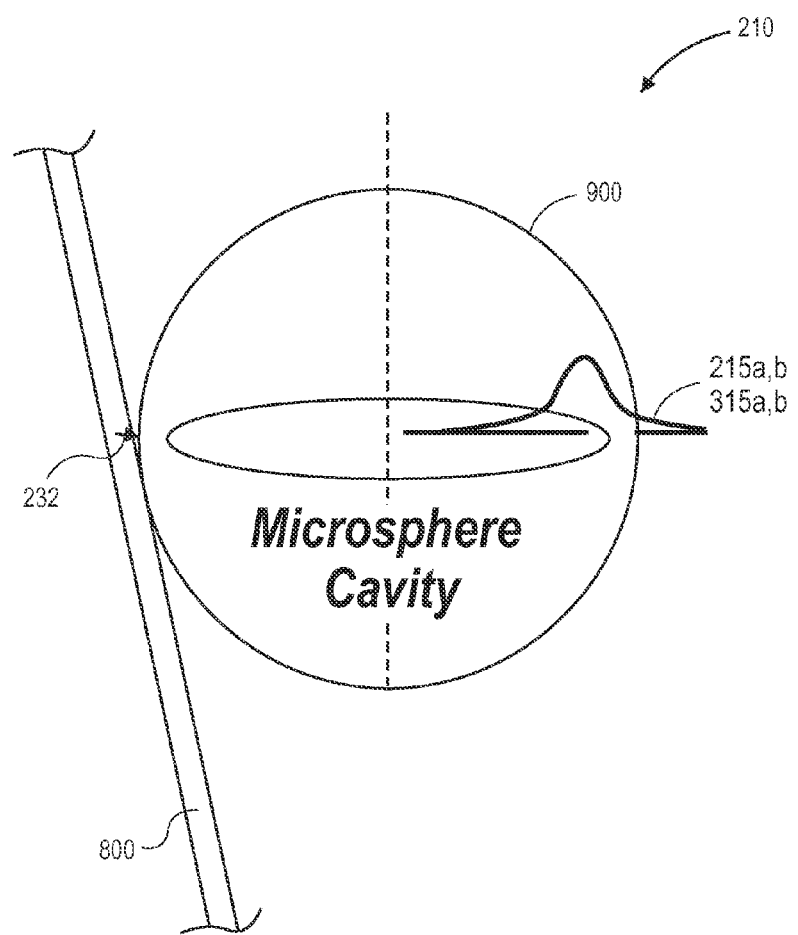
FIG. 9 illustrates a non-planar, spherical resonant microcavity that may be utilized in embodiments.

Further, while embodiments may be implemented using toroid-shaped micro-cavities 510 as shown in FIG. 5, embodiments may also be implemented using micro-cavities 210 having other shapes including spherical microcavities 900 as illustrated in FIG. 9 and described with further reference to U.S. Pat. No. 6,583,399, the contents of which were previously incorporated herein by reference. While the microcavity 210 can provide both high and ultra-high Q values as previously defined and be different shapes, this specification, refers to a microcavity 210 generally or a toroid-shaped micro-cavity 510 for ease of explanation.

Figure 10:
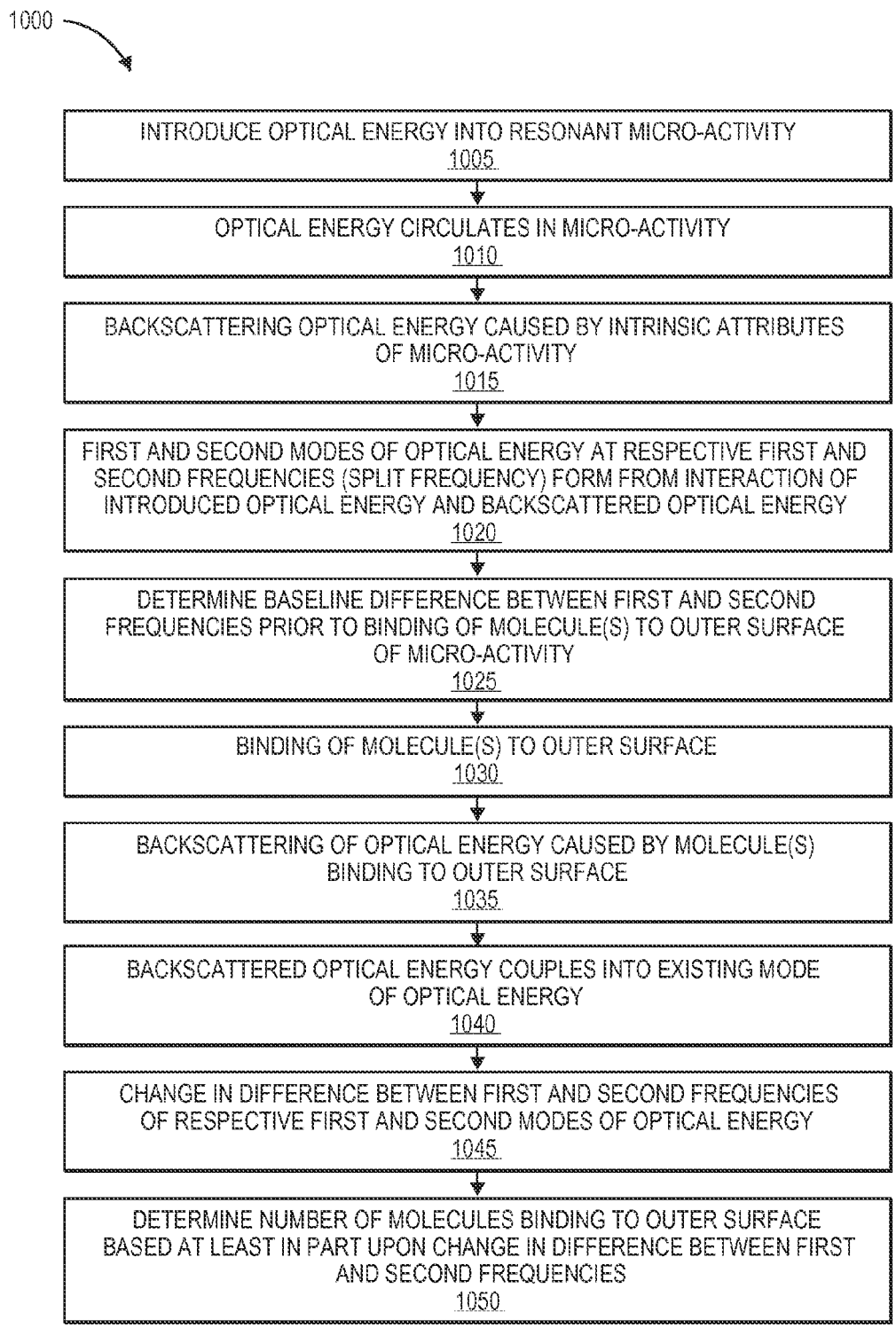
FIG. 10 is a flow chart of one embodiment of a method for detecting one or more molecules that bind to an outer surface of a resonant micro-cavity utilizing split frequency analysis and comparing how split frequency changes relative to a baseline split frequency difference.
Figure 11A:
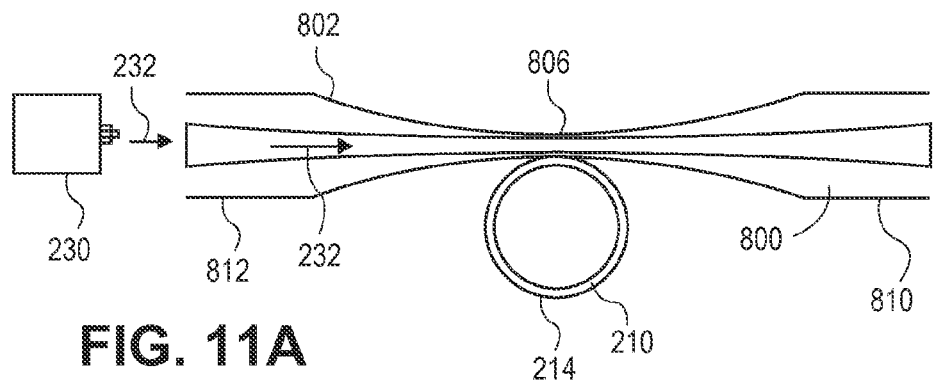
FIGS. 11A-G illustrate various steps of the method illustrated in FIG. 10 and how first and second modes at respective first and second frequencies may be formed by interaction of introduced and backscattered optical energy.
Figure 11B:
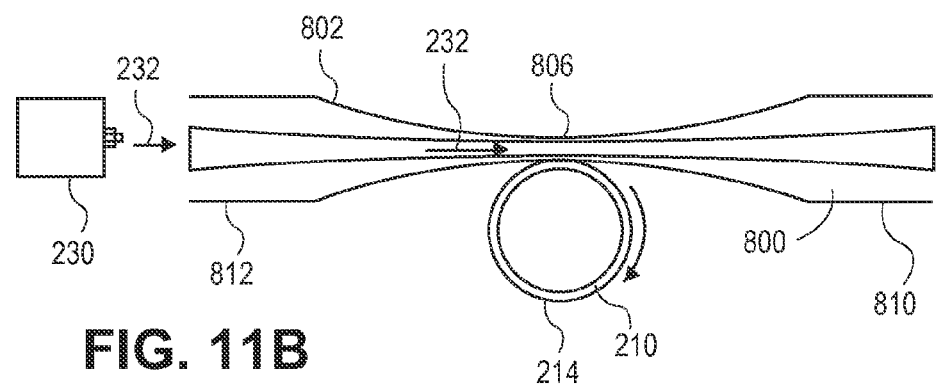

Having described aspects embodiments and aspects of micro-cavities 210 that may be utilized therein, further aspects of methods and systems according to embodiments are described with reference to FIG. 10, and with further reference to FIGS. 11A-G, a method 1000 of detecting a molecule 212 that binds to an outer surface 214 of a microcavity 210 includes, at step 1005, introducing optical energy 232 into the microcavity 210 (as illustrated in FIG. 11A) such that at step 1010, optical energy 232 circulates within the microcavity 210 (as shown in FIG. 11B). Embodiments may be implemented using various sources 230 and wavelengths of optical energy 232, including wavelengths in the visible spectrum such as 620-750 nm.

Figure 11C:
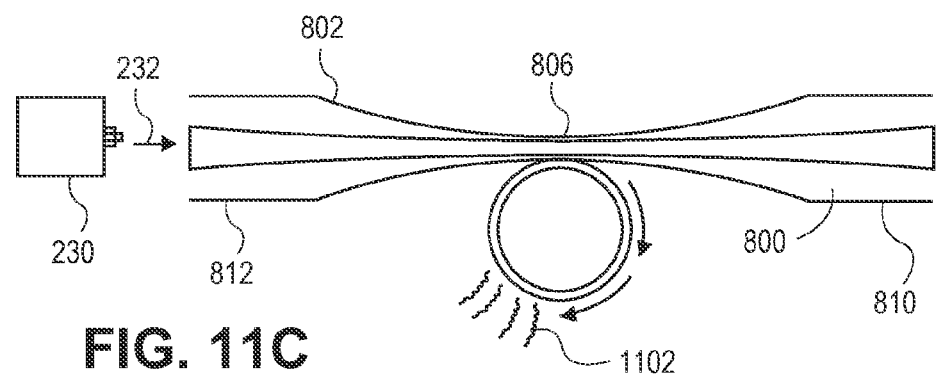
Figure 11D:
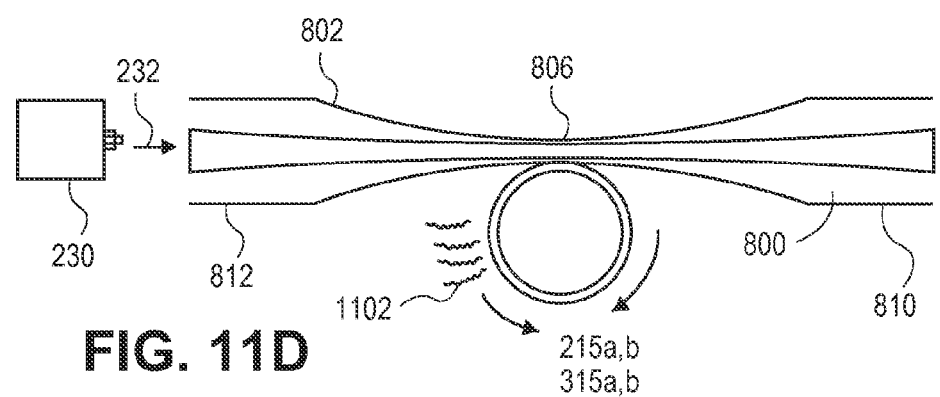

Referring again to FIG. 10, at step 1015, optical energy that circulates within the microcavity 210 backscatters 1102 in a second or opposite direction (as generally illustrated in FIG. 11C), e.g., due to intrinsic properties of the microcavity 210. At step 1020, first and second modes 215*a*, 215*b* (split modes) at respective first and second frequencies 315*a*, 315*b* (split frequency) are generated as a result of interaction of introduced and backscattered optical energy circulating within the microcavity 210, assuming the backscattered optical energy 1102 has sufficient intensity to overcome microcavity 210 losses (as shown in FIG. 11D). Thus, the optical energy resonating within the microcavity 210 has a first mode 215*a* at a first frequency 315*a*, and a second mode 215*b* at a second frequency 315*b*.

More particularly, counter-propagating introduced and backscattered optical energy are orthogonal such that if they do not interact each other, their resonance frequencies are the same. In embodiments of the invention, however, these counter-propagating modes interact with each other, thereby causing mode renormalization and two new orthogonal modes, i.e., a first mode 215*a* at a first frequency 315*a* and a second mode 215*b* at a second frequency 315*b*, otherwise referred to as split modes having split frequency 315 or mode doublets having frequencies 315*a*, 315*b*.

Each of the first and second modes 215*a*, 215*b* has a distinct resonance frequency, and both of the modes 215*a*, 215*b* are present in the both of the forwards and backwards directions. Thus, detecting a signal in one direction, e.g., the forward direction or the backwards direction, will result in detection of the split frequency or double dip structure generally illustrated in FIG. 3. The difference between these frequencies 315*a*, 315 or dips is proportional to the frequency split. Further aspects of split frequency or mode doublets are described in "Rayleigh scattering in high-Q microspheres," Optical Society of America, Vol. 17, No. 6, pp. 1051-1057 (2000) and "Splitting of high-Q Mie modes induced by light backscattering in silica microspheres," Optics Letters, Vol. 20, No. 18, pp. 1835-1837 (1995), the contents of which are incorporated herein by reference.

Figure 11E:
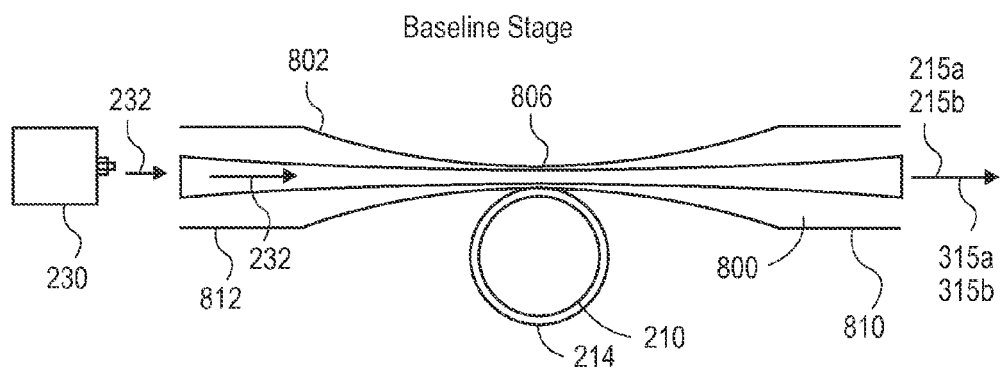

The first and second modes 215*a* and 215*b* having respective first and second frequencies f1 (315*a*) and f2 (315*b*) establish a baseline frequency difference 1104, i.e., a difference between the first and second frequencies 315*a* and 315*b*, otherwise referred to as a baseline split frequency difference (as shown in FIG. 11E).

The backscattering effect 1102 is a result of and the baseline difference 1104 is determined based at least in part upon optical energy 132 interacting with or being affected by intrinsic attributes of microcavity 210 within the microcavity 210 material or on the outer surface 214. For example, backscattering 1102 may be caused by Rayleigh scattering and certain microcavity 210 irregularities or defects such as material a shape irregularity, a material impurity and a micro-defect of the microcavity 210. During fabrication of a toroid-shaped microcavity 510, the toroid-shaped microcavity 510 may not be perfectly shaped as a toroid and instead may have a small degree of ellipticity. This may result from, for example, uneven reflow of the silica material or uneven application of heat during the reflow process. As another example, micro-defects such as cracks, material impurities and dust or particles within or on the outer surface 214 of the microcavity 210 may result in backscattering 1102 of the optical energy 132. The result of these intrinsic microcavity 210 material or structural characteristics is backscattering 1102 of the optical energy 232 that was initially introduced into the microcavity 210.

Thus, in certain embodiments, backscattering 1102, which leads to the interaction of counter-propagating introduced and backscattered optical energy and formation of first and second modes 215*a*, 215*b* having split frequencies 315*a*, 315*b* may result from natural, random imperfections or variations of the microcavity 210. In other embodiments, backscattering 1102 may also be invoked or intentionally induced.

For example, referring to FIGS. 12A-E, in one embodiment, a defect such as an aperture, hole or divot 1202 is formed within the outer surface 124 of the microcavity 210 using a source of energy such as a focused ion beam. This aperture 1202 is preferably large enough to induce backscattering 1102, but not so deep so as to allow too much optical energy to leak from the microcavity 210, which leads to significantly reducing the Q value and resonance time of optical energy in the microcavity 210. The width and depth of an aperture 1202 for this purpose may depend in part upon factors such as the dimensions, shape and material of the microcavity 210.

Figure 12D:
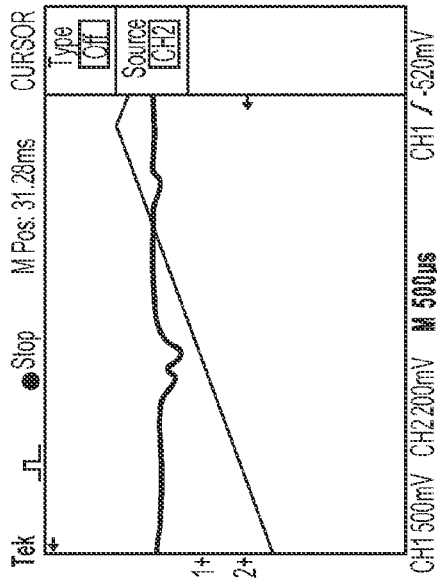
Figure 12E:
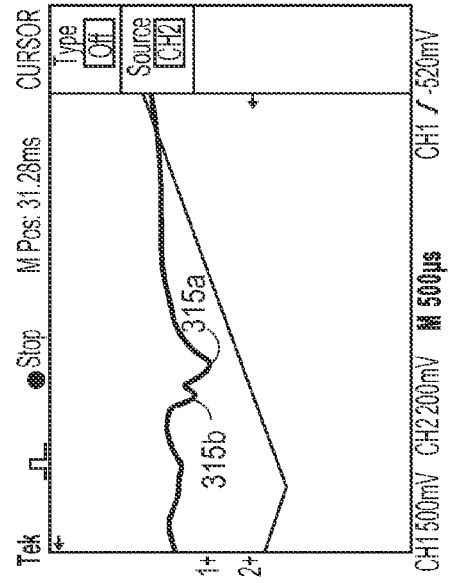
Figure 12C:
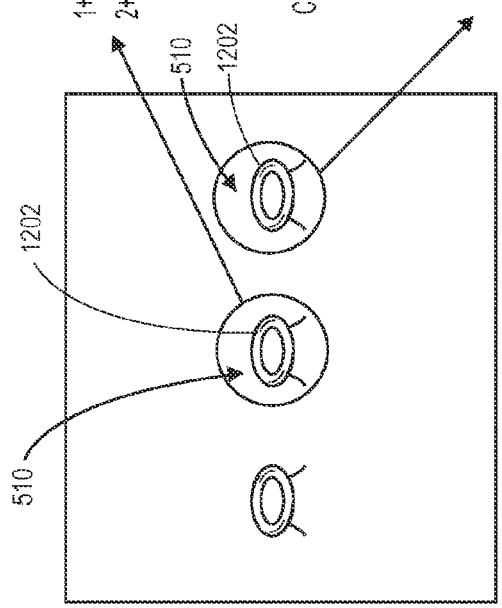
Figure 12F:
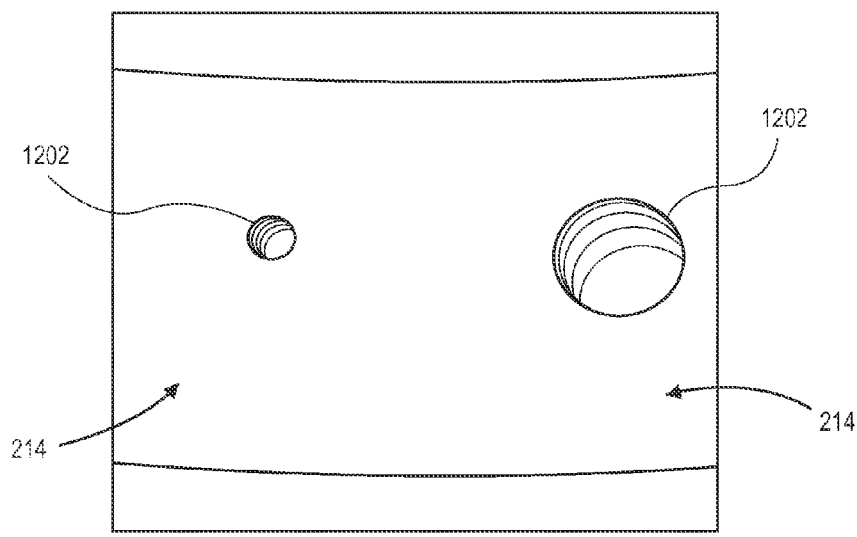

FIGS. 12A-D illustrate apertures or divots 1202 formed within a toroid-shaped microcavity 510. It was determined that apertures or divots 1202 having a diameter of about 50 nm (the apertures 1202 shown in FIGS. 12A-C and the smaller aperture in FIG. 12F) and fabricated using a 10 pA focused ion beam for about 5 seconds were able to induce split frequency 315 with acceptable Q value reductions, whereas apertures 1202 having a diameter of about 500 nm (the larger aperture 1202 shown in FIG. 12F) and formed using a 0.30 nA focused ion beam for about 15 seconds were too large due to an unsatisfactory Q value reduction. FIGS. 12D-E illustrates respective split frequency 315 data of two different microcavities 210 having an aperture 1202 formed using a focused ion beam.

Other embodiments for inducing backscattering 1102 and to induce formation of split frequency 315 may involve, for example, application of a nano-particle to the outer surface 124, e.g., utilizing an optical tweezer to apply a quantum dot to the outer surface 124. More specifically, a quantum dot can be connected to a glass or polystyrene bead via a DNA strand or other suitable connector. The quantum dot is applied to the outer surface 124 by using an optical tweezer to grasp the bead and bring the quantum dot into proximity to the outer surface 124 such that the quantum dot binds to the outer surface 124. The DNA connection can then be cleaved to release the quantum dot. Other embodiments of inducing backscattering 1102 may involve placing the microcavity 210 in dilute solutions such that molecules 212 in the solution bind to the outer surface 124.

Further, split frequency modes 215*a*, 215*b* may be generated by an active source such as a toroid laser, one example of which is a doped silica toroid-shaped micro-laser. According to one embodiment, a toroid-shaped microcavity 510 is doped with ytterbium. This particular microcavity laser may function in air and may also function when submerged in water. With these and other types of microcavity lasers, one source of optical energy at a first wavelength or frequency 315*a* is used as a pump, and the microcavity laser output is at second wavelength or frequency 315*b*.

In certain embodiments that utilize active components, split frequency 315 can be achieved by doping rather than forming an aperture or divot 1202 with the outer surface 214 of the microcavity 210. Further aspects of an example of a ytterbium-doped silica microcavity laser that may be utilized in embodiments, and that may bar particularly suitable for detection of a small number of molecules, including a single molecule, in air and water environments is described in further detail in "Yb-doped glass microcavity laser operation in water," by Eric Ostby and Kerry J. Vahala, published in Optics Letters, Vol. 34, No. 8, pp. 1153-1155 (April, 2009). The contents of which are incorporated herein by reference as though set forth in full.

While it will be understood that various methods and systems may be utilized to induce backscattering 1102, for ease of explanation, reference is made to naturally occurring backscattering 1102 due to one or more or all of Rayleigh scattering, shape and material irregularities or micro-defects, but that induced backscattering 1102 can be achieved utilizing various methods and systems to form a defect or to induce a small perturbation of the optical energy 232 resonating within the microcavity 210.

Referring again to FIGS. 10 and 11E, having established first and second modes 215*a*, 215 at respective first and second frequencies 315*a*, 315*b*, at step 1025, a baseline difference 1104 between the first and second frequencies 315*a*, 315*b*, or the magnitude of the split frequency 315, is determined. The baseline difference 1104 is based on the difference between the first and second frequencies 315*a*, 315*b* before molecules 212 bind to the outer surface 214. The baseline difference 1104 may be due to intrinsic properties or attributes of the microcavity 210 such as one or more or all of Rayleigh scattering and other factors such as shape irregularities (e.g., if a toroid-shaped microcavity has a certain degree of ellipticity), material impurities and micro-defects, and may also be intentionally formed as discussed above. The baseline difference 1104 may also be determined based on a split frequency generated by an active source such as a toroid laser as discussed above.

Figure 11F:
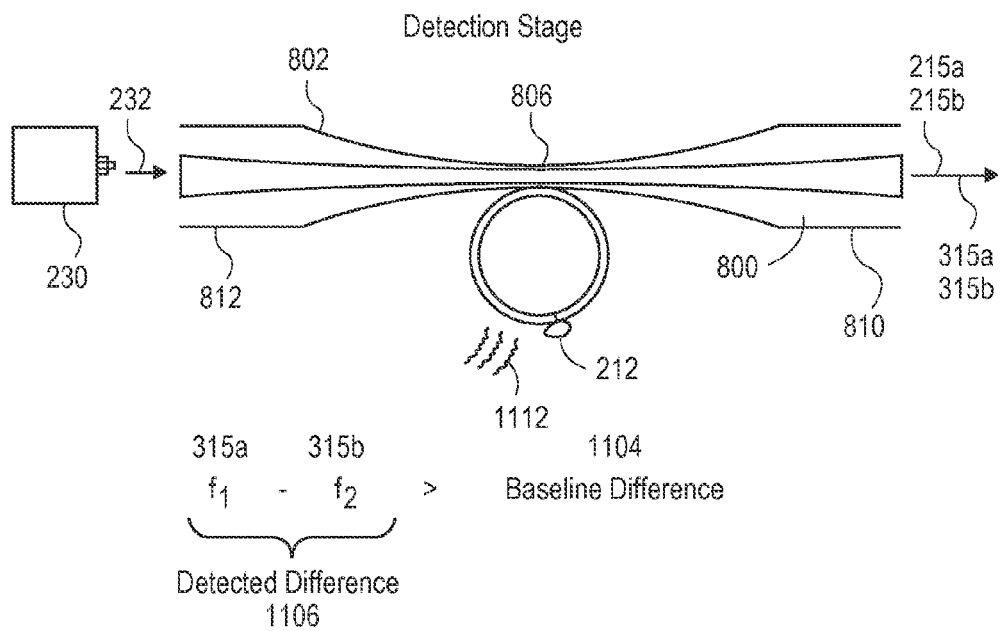
Figure 11G:
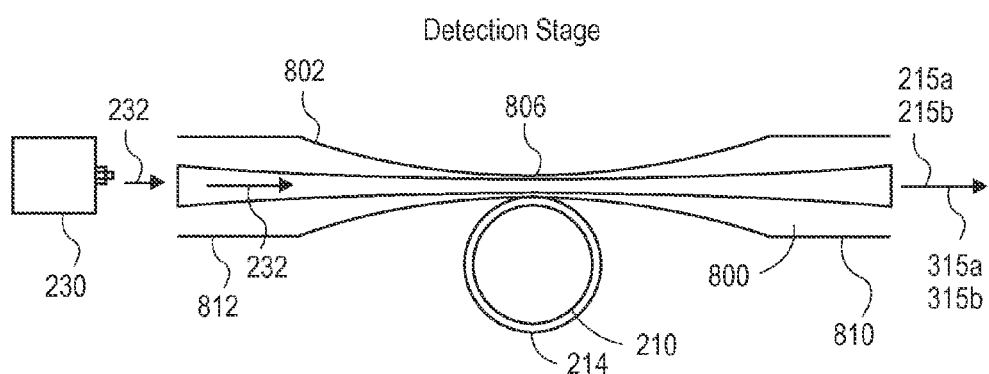

At step 1030, during a detection stage, optical energy 232 is coupled into the microcavity 210 and target biological or chemical molecules 212 bind to the outer surface 214 of the microcavity 210 (as shown in FIG. 11F) which, in turn, causes optical energy 232 that circulates within the optical cavity 210 to be backscattered 1112. At step 1035, backscattered energy 1102 is coupled into at least one of the modes, e.g., the second mode 125*b* at step 1040 (as shown in FIG. 11G). At step 1045, this results in a change 1108 of the frequency difference from the initial or reference baseline difference 1104 to a larger, detection difference 1106 between the first and second frequencies 315*a*, 315*b* due to one or more molecules 212 binding to the outer surface 214. At step 1050, a processing element determines the number of molecules 212 binding to the outer surface 214 based at least in part upon the change 1108.

The change 1108 of the frequency difference as represented by the detected frequency difference 1106 compared to the baseline difference 1104 can be measured utilizing an oscilloscope 260 or other type of display or processing element. Referring again to FIG. 2, detection of the split frequency change 1108 can be performed by scanning the wavelength of the laser or source 230 utilizing the function generator 270 and detecting the power that is transmitted out of the microcavity 210 in synchronization with the waveform generated by the function generator 270 with the oscilloscope 260. In this manner, each point of the time axis displayed by the oscilloscope 260 represents a distinct wavelength or frequency. In the case of embodiments, a split frequency 315*a*, 315*b* or two dips are shown in the display of the oscilloscope 260. Thus, using the function generator 270 and the oscilloscope 260 to measure the distance between the frequency dips 315*a*, 315*b* indicates the detected split frequency difference 1106 between the modes 215*a*, 215*b* of optical energy relative to the baseline difference 1104 which, in turn, indicates molecule 212 binding events.

Figure 13:
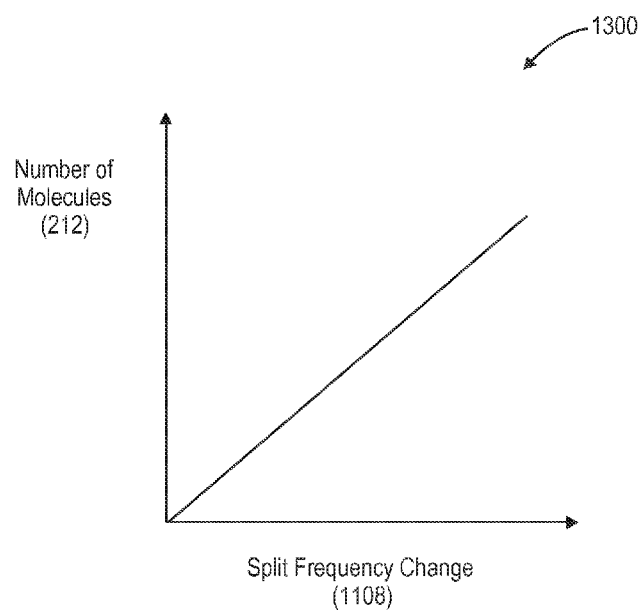
FIG. 13 is a graph that generally illustrates how embodiments may be used to determine a number of molecules that bind to a microcavity outer surface based on a change of the split frequency compared to a baseline split frequency difference.

For example, as generally illustrated in FIG. 13, determining the number of molecules 212 that bind to the outer surface 214 may be performed utilizing a chart or relational data structure that indicates how many molecules 212 bind to the outer surface 214 (y axis) based on a split frequency change 1108 (x axis), or the change of the detected split frequency difference 1006 compared to the baseline difference 1104. According to one embodiment, chart data is determined empirically by testing various micro-cavities 210 and fluids having different concentrations of molecules 212 such that subsequent split frequency measurements can be compared to the previously prepared chart 1300 to determine the number of molecules 212 that bind to the outer surface 214. It should be understood that data indicating how many molecules 212 bind to the outer surface based on a detected split frequency change 1108 may not be perfectly linear as shown in FIG. 13, and FIG. 13 is provided to generally illustrate the relationship between split frequency changes 1106 and the number of molecules 212 detected.

Figure 14:
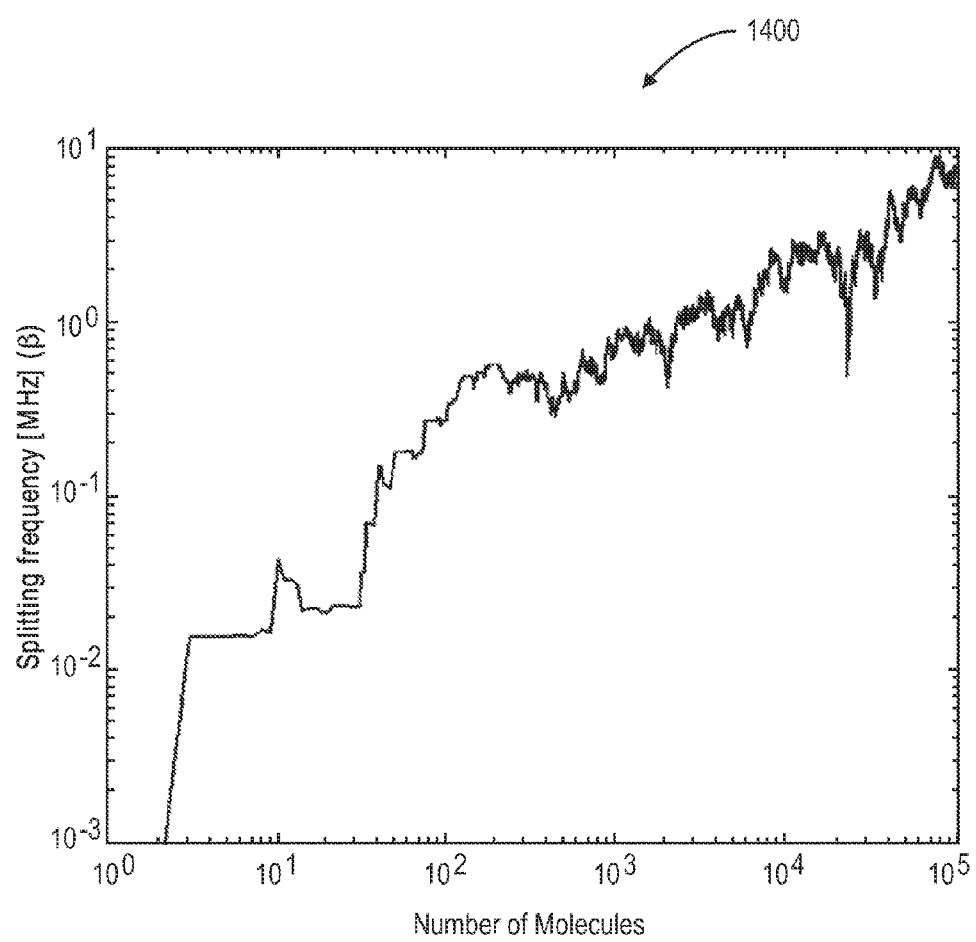
FIG. 14 is a graph illustrating a numerical simulation of a split frequency change expression.

In another embodiment, changes 1106 of the frequency difference relative to the baseline difference 1104 can be used to determine the number of molecules 212 binding to the outer surface 214 based on the following expression:

$$\beta = \frac{\omega_0}{2} \frac{\int \sum_i \delta \in (r_i) E_+ E_-^* dv}{\int \in (r_i) E_+ E_+^* dv} + \beta_0$$

wherein $\beta$ is the difference between respective frequencies 315a, 315b of modes 215a, 215b due to binding of at least one molecule 212 to the outer surface 214, $\beta_0$ is a baseline difference 1104 between respective frequencies of modes 215a, 215b due to an intrinsic property of the microcavity 210, $\delta\epsilon(r_i)$ is a change of relative permittivity of the resonant microcavity 210 due to the at least one molecule 212 binding to the outer surface 214 at a spatial position $r_i$, $E_+$ is a first propagation mode 215a, $E_+^*$ is a complex conjugate of the first propagation mode 215a, and $E_-^*$ is a complex conjugate of a second propagation mode 215b. FIG. 14 includes a graph 1400 that illustrates results of a numerical simulation based on the above expression. The x-axis is the number of molecules 212, and the y-axis is the split frequency 315 (MHz) ($\beta$) such that a measured split frequency 315 can be correlated to a corresponding number of molecules 212 binding to the outer surface 214.

FIGS. 13 and 14 illustrate how changes in the frequency difference 1106 relative to the baseline difference 1104 may be utilized to determine the number of molecules 212 binding to the outer surface 214 and generally illustrate that as more molecules 212 bind to the outer surface 214, the frequency difference 1106 relative to the baseline difference 1104 increases. One embodiment involves a step-wise increase in the frequency difference 1106 as a molecule 212 binds to the outer surface 214.

FIG. 14 also illustrates certain instances when data in the graph decreases as more molecules 212 bind to the outer surface 214. These effects are believed to be due to the complex number nature of $\beta$ (the difference between respective frequencies 315a, 315b of first and second modes 215a, 215b due to binding of at least one molecule 212). It is believed that in certain instances, there will be constructive or destructive interference by adding one molecule 212 depending on its location on the microcavity 212, hence the occasional decrease. However, even with occasional decreases, the general trend illustrates that the frequency difference 1106 increases as more molecules 212 bind to the outer surface 214.

While embodiments may be utilized to detect how many molecules 212 are on the outer surface 214, embodiments may also be utilized to detect a single molecule 212 that binds to the outer surface 214, e.g., using a very sensitive microcavity 210 such as an ultra-high Q toroid 510 that has sufficiently high Q value for single molecule 212 detection. For example, when testing a low concentration fluid, e.g., having an attomolar concentration, target molecules 212 may arrive at the toroid-shaped microcavity 510 at different time intervals in a discrete random pattern (e.g., a Poinssonian pattern). As a result, the split frequency 315 will change from the baseline frequency 1104 difference to a larger frequency difference 1106 and will follow a Poinssonian distribution, which may be utilized to detect a single binding event on the outer surface 214 of the microcavity 510. Detection of single molecules 212 in a higher concentration fluid, e.g., having a micromolar concentration, may result in molecules 212 binding on the outer surface 214 in the same time interval. As a result, single molecule 212 detection may require a higher sampling rate oscilloscope 260. In the event that detection involves a relatively high concentration of molecules 212, the detector 250 and the oscilloscope 260 may be used to observe a continuous increase of the split frequency 315 up to a saturation point.

Figure 15A:
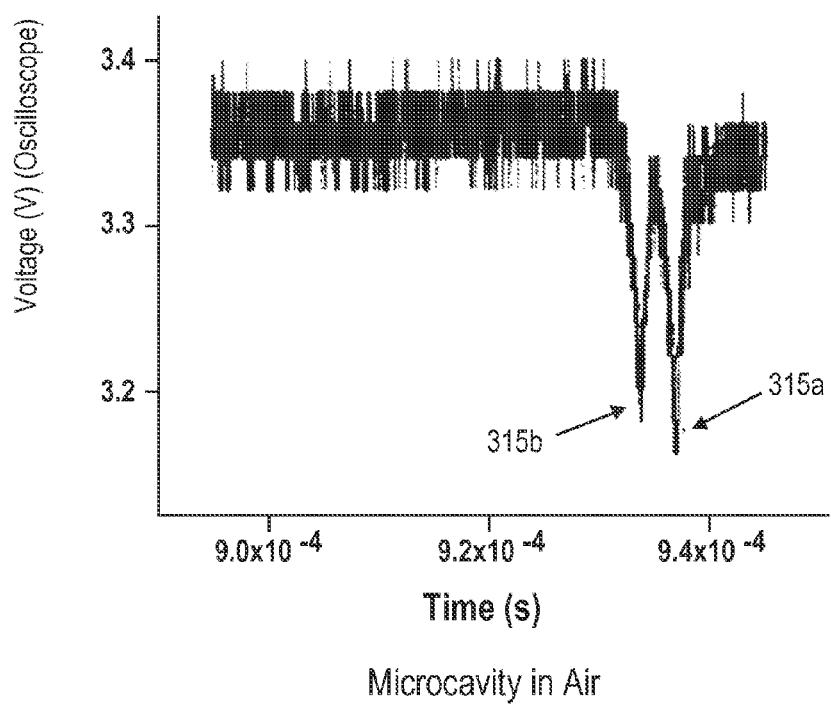
FIGS. 15A-H are graphs demonstrating effectiveness of embodiments and illustrating a baseline split frequency difference, how the split frequency difference increases due to binding of unlabeled IL-2 to an outer surface of a microcavity, and how the split frequency difference decreases due to injection of glycine that unbinds the IL-2 from the outer surface.
Figure 15B:
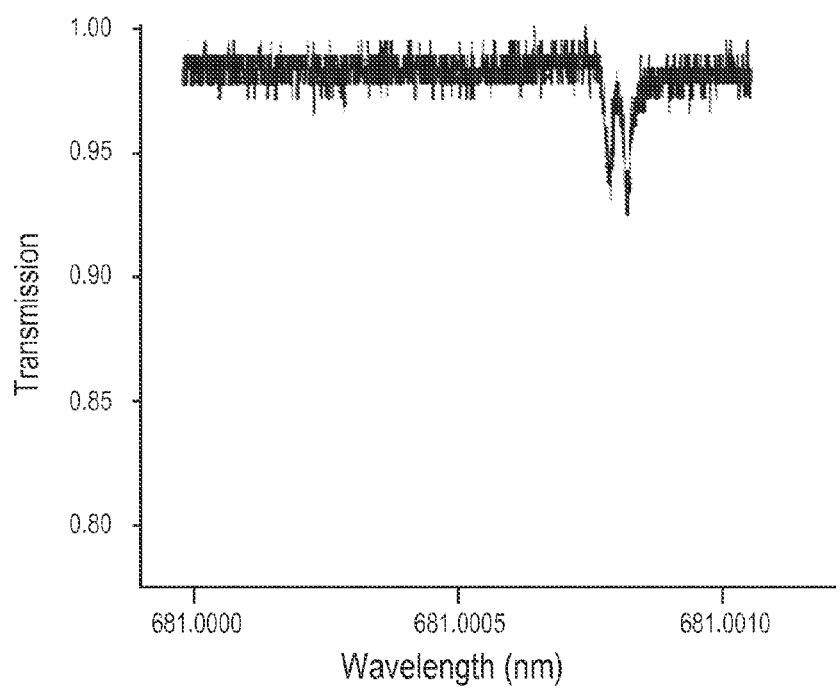
Figure 15C:
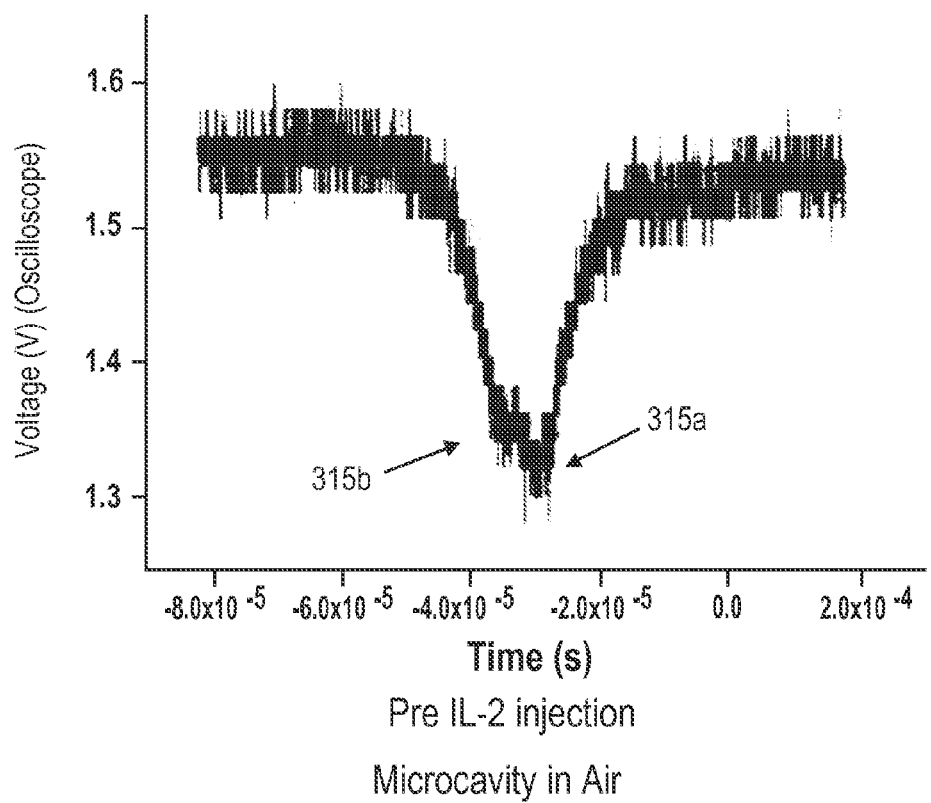
Figure 15D:
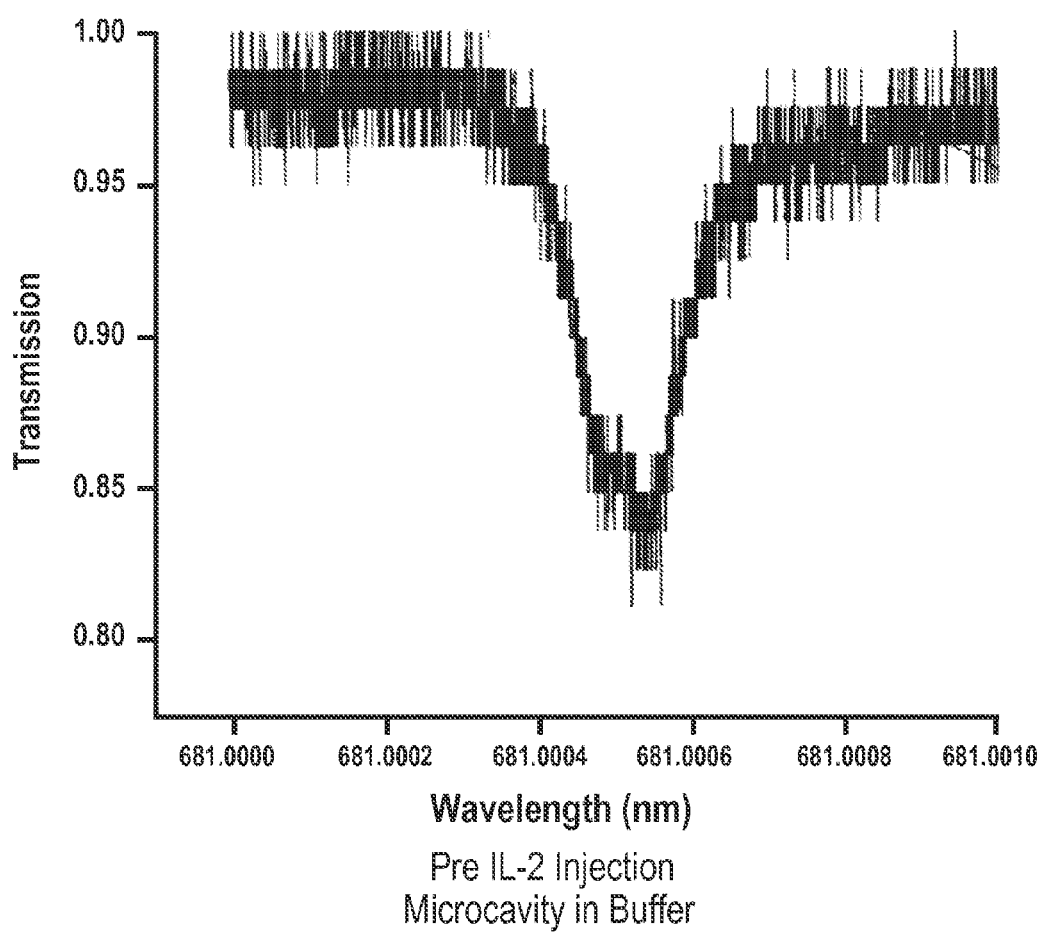

Referring to FIGS. 15A-H, a test was conducted to demonstrate the effectiveness of utilizing changes 1106 in the split frequency 315 to determine binding of molecules 212 to a silica toroid-shaped microcavity 510 (as shown in FIGS. 5-8C). The test involved initially characterizing the split frequency 315 of the microcavity 510 in air (as shown in FIGS. 15A-B), and then immersing the microcavity 510 in HEPES buffer (4-(2-hydroxyethyl)-1-piperazineethanesulfonic acid) to determine a baseline frequency difference 1104 caused by intrinsic microcavity 510 properties such as Rayleigh scattering, micro-defects, etc. within the buffer (as shown in FIGS. 15C-D).

FIGS. 15A-B are graphs illustrating a split frequency difference 1104 when the micro-cavity 510 before the microcavity 510 is placed in a buffer. FIG. 15A illustrates data with respect to time (s) (x-axis) (certain times are negative due to the reference point of the oscilloscope 260 that was utilized) and voltage (as read from the oscilloscope 260) (y-axis), and FIG. 15B illustrates the same data as shown in FIG. 15A but the data is characterized in terms of wavelength (inverse of frequency) (x-axis) and transmission (y-axis).

FIGS. 15C-D are graphs of data resulting from placing the micro-toroid-shaped microcavity 510 in buffer coupling optical energy 232 into the microcavity 510. The result observed using the function generator 270 and the oscilloscope 260 was a baseline frequency difference 1104 of about 46 MHz. FIG. 15C illustrates a baseline split frequency difference 1104 data in terms of time (s) (x-axis) (certain times are negative due to the reference point of the oscilloscope 260 that was utilized) and voltage (as read from the oscilloscope 260) (y-axis), and FIG. 15D illustrates the same data as shown in FIG. 15C but characterized in terms of wavelength (inverse of frequency) (x-axis) and transmission (y-axis).

Figure 15E:
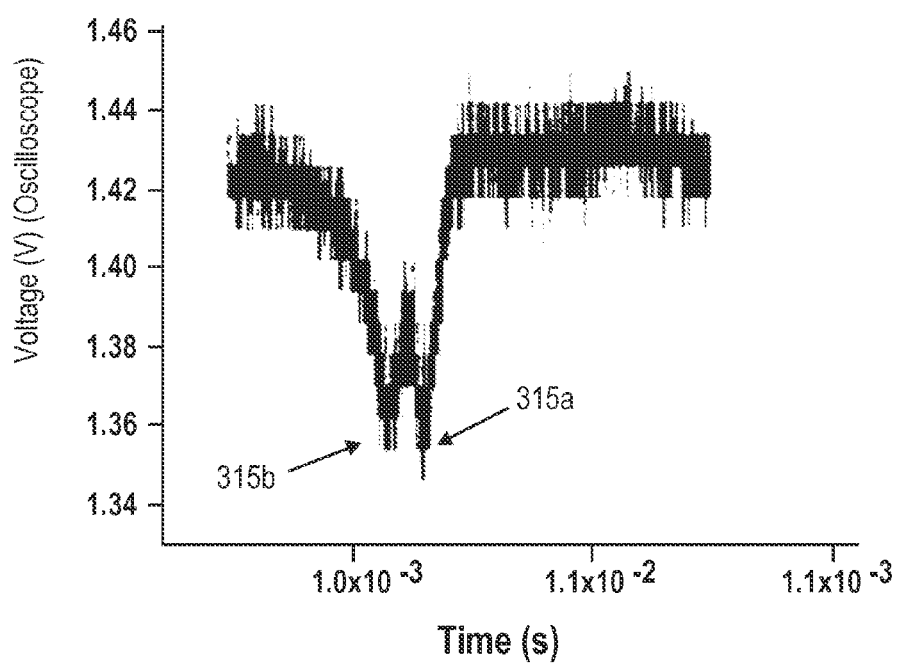
Figure 15F:
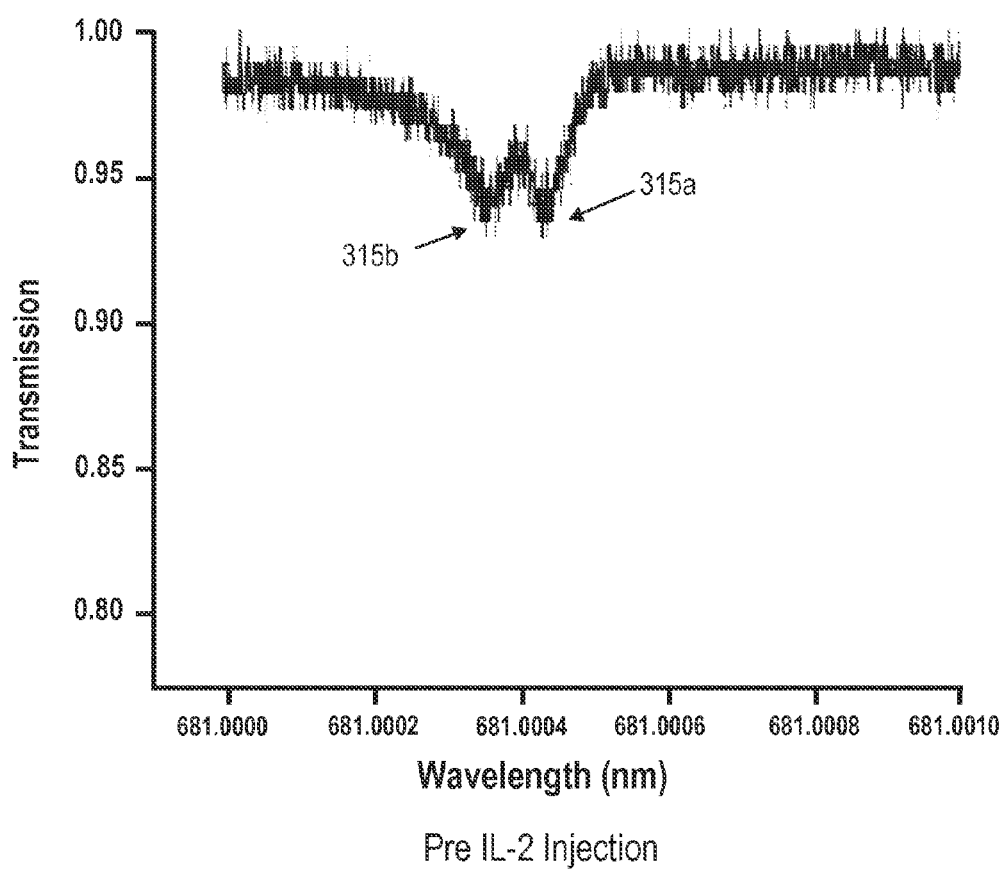
Figure 15G:
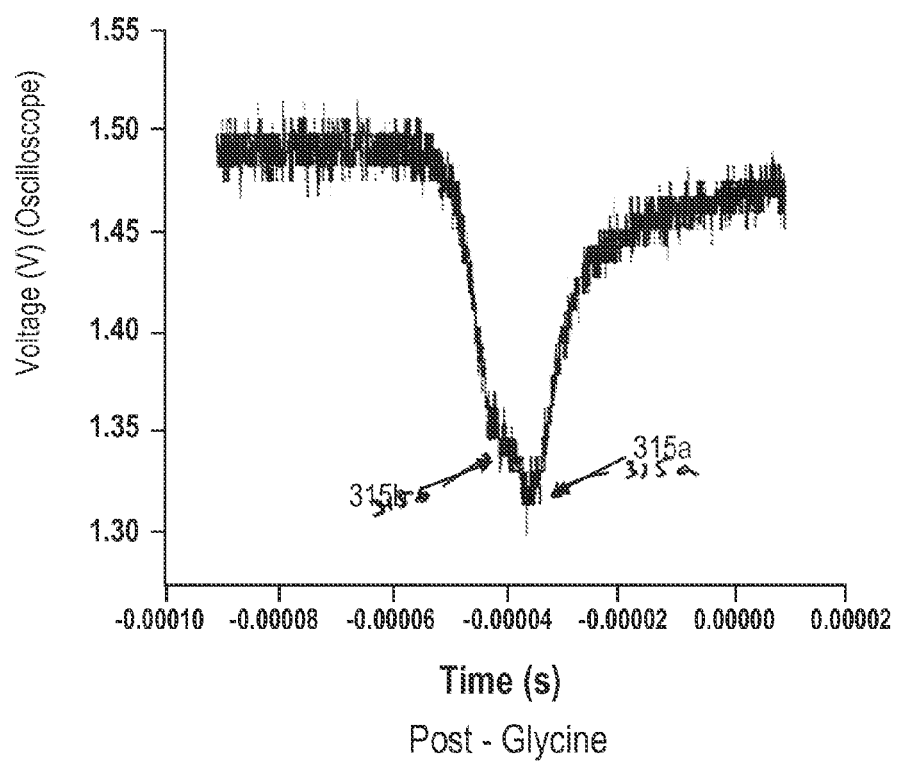
Figure 15H:
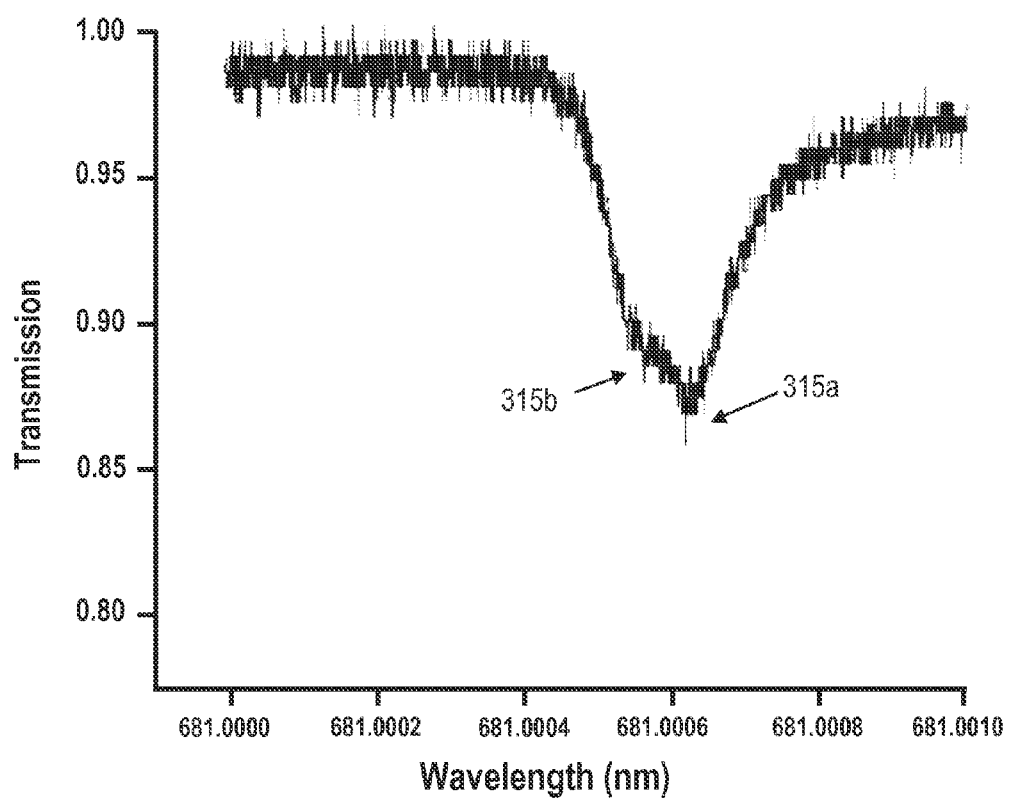

The next step of the test was injection of a first solution of buffer having about 0.1 micromolar concentration of protein G and an antibody against IL-2 in order to functionalize the outer surface 214 of the microcavity 510. A second solution of including a target antigen molecule 212 of unlabeled Interleukin-2 (IL-2) was then injected into the environment. The results of monitoring the frequency difference 315 after injection of IL-2 are shown in FIGS. 15E-F, which show how the detected split frequency 1506 increased from the baseline difference 1104 of 46 MHz to about 277 MHz. FIG. 15E illustrates the split frequency difference resulting from IL-2 injection in terms of time (s) (x-axis) and voltage (as read from the oscilloscope 260) (y-axis), and FIG. 15F illustrates the same data as shown in FIG. 15E but characterized in terms of wavelength (inverse of frequency) (x-axis) and transmission (y-axis).

After injection of unlabeled IL-2, a solution having about a 10 millimolar concentration of Glycine was then injected into the environment. The result of Glycine injection was Glycine binding IL-2 to remove or unbind IL-2 from the outer surface 214, thereby resulting in the detected frequency difference 1106 reducing from 277 MHz to about 92 MHz, thus demonstrating that IL-2 molecules binding to the outer surface 214 caused the detected frequency difference 1106 to increase expand whereas when IL-2 molecules were released from the outer surface 214, the detected frequency difference 1106 decreased. FIG. 15G illustrates the change in terms of time (s) (x-axis) (certain times are negative due to the reference point of the oscilloscope 260 that was utilized) and voltage (as read from the oscilloscope 260) (y-axis), and FIG. 15H illustrates the same change as shown in FIG. 15G but characterized differently in terms of wavelength (inverse of frequency) (x-axis) and transmission (y-axis).

FIGS. 15G-H illustrate that in this particular test, the split frequency 315 reduced from 277 MHz to 92 MHz rather than to the original or baseline difference of 46 MHz. It is believed that this is a result of Glycine introducing additional impurities or particles that attached to the outer surface 214 while Glycine removes IL-2 from the outer surface 214 or that insufficient Glycine was added to remove the IL-2, thus resulting in some of the IL-2 molecules remaining on the outer surface 214.

It should be understood that although certain tests were performed utilizing IL-2 as a target molecule 212, embodiments may involve detection of various other labeled and unlabeled biological and chemical molecules 212 and numbers of molecules 212, and that the outer surface 214 may be functionalized, e.g., as described in one or more references previously incorporated herein by reference, to provide detection selectivity. High and ultra-high Q values provide for this selectivity coupled with sensitivities that are able to detect small numbers of molecules 212 including a single molecule 212.

Although references have been made in the foregoing description to various embodiments, persons of ordinary skill in the art will recognize that insubstantial modifications, alterations, and substitutions can be made to the described embodiments without departing from the invention as recited in the accompanying claims. For example, while certain embodiments are described with reference to silica micro-cavities, micro-cavities may be made of other materials and may be fabricated using methods other than the reflow methods described above. Further, other substrates besides silicon may be suitable depending on the particular application of the device and integration and coupling considerations. Moreover, various micro-cavities other than micro-toroids can be utilized to implement embodiments including spherical micro-cavities. Further, embodiments can be implemented using microcavity resonant sensors individually or embodiments may involve an array of sensors and may be integrated with other devices. Additionally, although embodiments that utilize a detection methods based on changes of a split frequency are described with reference to whispering gallery mode resonators, embodiments can also be implemented with other resonators that are not WGM resonators. Additionally, it should be understood that embodiments may involve passive micro-cavities or active microcavity lasers.

Additionally, it should be understood that the baseline split frequency and changes to the split frequency as molecules bind to an outer surface of a microcavity may vary from the examples discussed above depending on, for example, the wavelength of the source, the type, size, shape and material of the microcavity, the different intrinsic attributes of a microcavity including different Rayleigh scattering, micro-defects, shape irregularities, the environment in which the microcavity operates, the target molecule, the concentration of the target molecule in a solution, the cavity linewidth or Q value, control techniques, etc. Thus, it should be understood that the baseline split frequency may be smaller or larger than the baseline frequencies discussed above (e.g., about 46 MHz in the test performed) and detectable changes of a frequency difference relative to a baseline frequency difference may be smaller or larger than the examples discussed above (e.g., about 230 MHz in the test perfo med).

Further, while various numeric simulations and expressions are provided in order to describe how binding of target molecules results in a split frequency change, persons skilled in the art will appreciate that embodiments may involve different numeric simulations and expressions, and that these simulations and expressions are provided to describe certain ways in which embodiments may be utilized in a non-limiting manner.

What is claimed is:

1. A method for detecting a molecule, the method comprising:

introducing optical energy into a resonant microcavity, the optical energy circulating within the resonant microcavity;

before detection, determining a first frequency of a first mode and a second frequency of a second mode of optical energy circulating within the resonant microcavity;

determining a pre-detection difference between the first frequency and the second frequency; and detecting at least one molecule that binds to an outer surface of the microcavity based at least in part upon how the pre-detection difference changes to a detection difference between the first frequency and the second frequency due to the at least one molecule binding to the outer surface, the detection difference being expressed as $$\beta = \frac{\omega_0}{2} \frac{\int \sum_i \delta\epsilon(r_i) E_+ E_-^* dv}{\int \epsilon(r_i) E_+ E_+^* dv} + \beta_0$$

wherein

β is the detection difference between the first and second frequencies due to binding of at least one molecule to the outer surface, $\beta_0$ is the pre-detection difference between the first and second frequencies due to an intrinsic property of the micro cavity, $\delta\epsilon(r_i)$ is a change of relative permittivity of the microcavity due to the at least one molecule binding to the outer surface at a spatial position $r_i$, $E_+$ is a forward propagation mode, $E_+^*$ is a complex conjugate of the forward propagation mode, and $E_-^*$ is a complex conjugate of a backward propagation mode.

2. The method of claim 1, where at least one of the first and second modes is generated by interaction of counter-propagating modes of optical energy within the resonant micro cavity.

3. The method of claim 1, the pre-detection difference being based at least in part upon an intrinsic property of the resonant microcavity.

4. The method of claim 3, the intrinsic property comprising Rayleigh scattering of the resonant microcavity.

5. The method of claim 3, the intrinsic property comprising at least one of the properties selected from the group consisting of a shape irregularity, a material impurity and a micro-defect of the resonant microcavity.

6. The method of claim 1, wherein at least one of the first and second modes of optical energy is generated as a result of optical energy being introduced into the microcavity, at least a portion of the introduced optical energy backscattering, the introduced and backscattered optical energy interacting with each other to form at least one of the first and second modes.

7. The method of claim 1, further comprising forming a defect within the resonant microcavity to induce formation of first and second modes of optical energy having respective first and second frequencies.

8. The method of claim 7, wherein the defect induces backscattering of optical energy that is introduced into the resonant micro-cavity, introduced and backscattered optical energy interacting with each other to form at least one of the first and second modes.

9. The method of claim 8, forming the defect comprising applying a focused ion beam energy to the outer surface of the microcavity to form an aperture or divot within the resonant microcavity.

10. The method of claim 1, the detection difference increasing relative to the pre-detection difference as additional molecules bind to the outer surface.

11. The method of claim 1, wherein a single, unlabeled molecule is detected by binding to a functionalized outer surface of the resonant microcavity, the functionalized outer surface comprising an antibody, an antigen or a protein.

12. The method of claim 1, detecting the at least one molecule being insensitive to frequency jitter of a source of the optical energy.

13. The method of claim 1, the optical energy resonating within a passive resonant micro cavity.

14. The method of claim 1, the optical energy resonating within an active resonant micro cavity.

15. The method of claim 1, detecting the at least one molecule comprising detecting a biological molecule or a chemical molecule.

16. The method of claim 1, detecting at least one molecule comprising detecting at least one molecule that binds to an outer surface of a planar resonant microcavity supported by a substrate.

17. The method of claim 1, detecting at least one molecule comprising detecting at least one molecule that binds to an outer surface of a planar, toroid-shaped resonant microcavity supported by a substrate, an outer edge of the planar, toroid-shaped resonant microcavity extending outwardly beyond an outer edge of the substrate.

18. The method of claim 1, wherein optical energy is introduced into a resonant microcavity having a Q value greater than $10^7$.

19. The method of claim 1, wherein the detection difference is greater than the pre-detection difference.

20. The method of claim 1, wherein a number of molecules that bind to the outer surface is detected based at least in part upon a difference between the detection difference and the pre-detection difference.

21. A method for detecting at least one molecule, the method comprising:
introducing optical energy into a resonant microcavity having a functionalized outer surface;
before detection, determining a first frequency of a first mode and a second frequency of a second mode of optical energy circulating within the resonant microcavity;
determining a pre-detection difference between the first frequency and the second frequency, the pre-detection difference being based at least in part upon an intrinsic property of the resonant microcavity before a molecule binds to the outer surface; and
during a detection stage, monitoring the first and second frequencies and detecting at least one molecule that binds to the functionalized outer surface based at least in part upon how the pre-detection difference changes to a detection difference between the first frequency and the second frequency due to binding of the at least one molecule to the outer surface, the detection difference being expressed as $$\beta = \frac{\omega_0}{2} \frac{\int \sum_i \delta\epsilon(r_i) E_+ E_-^* dv}{\int \epsilon(r_i) E_+ E_+^* dv} + \beta_0$$

wherein
$\beta$ is the detection difference between the first and second frequencies due to binding of at least one molecule to the outer surface,
$\beta_0$ is the pre-detection difference between the first and second frequencies due to an intrinsic property of the resonant microcavity,
$\delta\epsilon(r_i)$ is a change of relative permittivity of the resonant microcavity due to the at least one molecule binding to the outer surface at a spatial position $r_i$,
$E_+$ is a forward propagation mode,
$E_+^*$ is a complex conjugate of the forward propagation mode, and
$E_-^*$ is a complex conjugate of a backward propagation mode.

22. The method of claim 21, where at least one of the first and second modes is generated by interaction of counter-propagating modes of optical energy within the micro-cavity.

23. The method of claim 21, wherein at least one of the first and second modes of optical energy is generated as a result of optical energy being introduced into the microcavity, at least a portion of the introduced optical energy backscattering, the introduced and backscattered optical energy interacting with each other to form at least one of the first and second modes.

24. The method of claim 21, the pre-detection difference being based at least in part upon Rayleigh scattering, a shape irregularity, a material impurity or a micro-defect of the resonant microcavity.

25. The method of claim 21, further comprising forming a defect within the resonant microcavity to induce formation of first and second modes of optical energy having respective first and second frequencies.

26. The method of claim 25, wherein the defect induces backscattering of optical energy that is introduced into the resonant micro-cavity, the introduced and backscattered optical energy interacting with each other to form at least one of the first and second modes.

27. The method of claim 21, wherein the detection difference is greater than the pre-detection difference.

28. The method of claim 21, wherein a number of molecules that bind to the outer surface is detected based at least in part upon a difference between the detection difference and the pre-detection difference.

29. A method for detecting a molecule, the method comprising:

introducing optical energy into a resonant microcavity, the optical energy circulating within the resonant microcavity; and detecting at least one molecule that binds to an outer surface of the microcavity based at least in part upon how a difference between a first frequency and a second frequency of respective first and second modes of optical energy circulating within the resonant micro-cavity changes due to the at least one molecule binding to the outer surface, the difference between the first and second frequencies of respective first and second modes being expressed as $$\beta = \frac{\omega_0}{2} \frac{\int \sum_i \delta \in (r_i) E_+ E_-^* dv}{\int \in (r_i) E_+ E_+^* dv} + \beta_0$$

wherein $\beta$ is the difference between the first and second frequencies due to binding of at least one molecule to the outer surface, $\beta_0$ is a baseline difference between the first and second frequencies due to an intrinsic property of the microcavity, $\delta\epsilon(r_i)$ is a change of relative permittivity of the microcavity due to the at least one molecule binding to the outer surface at a spatial position $r_i$, $E_+$ is a forwards propagation mode, $E_+^*$ is a complex conjugate of the forwards propagation mode, and $E_-^*$ is a complex conjugate of a backwards propagation mode.

30. A method of detecting at least one molecule, the method comprising:

introducing optical energy into a resonant microcavity having a functionalized outer surface, wherein a first mode of optical energy having a first frequency and a second mode of optical energy having a second frequency circulate within the resonant microcavity;

determining a baseline difference, the baseline difference comprising a difference between the first and second frequencies due to an intrinsic property of the resonant microcavity before a molecule binds to the outer surface;

monitoring a difference between the first and second frequencies; and detecting at least one molecule that binds to the functionalized outer surface based at least in part upon how the difference between the first and second frequencies changes relative to the baseline difference due to binding of the at least one molecule to the outer surface, the difference between the first and second frequencies of respective first and second modes being expressed as $$\beta = \frac{\omega_0}{2} \frac{\int \sum_i \delta \in (r_i) E_+ E_-^* dv}{\int \in (r_i) E_+ E_+^* dv} + \beta_0$$

wherein $\beta$ is the difference between the first and second frequencies due to binding of at least one molecule to the outer surface, $\beta_0$ is the baseline difference between the first and second frequencies due to an intrinsic property of the resonant microcavity, $\delta\epsilon(r_i)$ is a change of relative permittivity of the resonant microcavity due to the at least one molecule binding to the outer surface at a spatial position $r_i$, $E_+$ is a forwards propagation mode, $E_+^*$ is a complex conjugate of the forwards propagation mode, and $E_-^*$ is a complex conjugate of a backwards propagation mode.

* * * * *